United States Patent
Furuya et al.

(10) Patent No.: US 7,459,477 B2
(45) Date of Patent: Dec. 2, 2008

(54) SUBSTITUTED N-PHENYL-PHENOXY NICOTINIC ACID-(THIO)AMIDES AND THEIR USE AS HERBICIDES

(75) Inventors: Takashi Furuya, Izumisano (JP); Minoru Yamaguchi, Osakasayama (JP); Masanori Tohnishi, Sakai (JP); Akira Seo, Hashimoto (JP); Masayuki Morimoto, Kawachinagano (JP); Tsuyoshi Takemoto, Kawachinagano (JP); Shinsuke Fujioka, Kawachinagano (JP)

(73) Assignee: Nihon Nohyaku, Co., Ltd., Tokyo (JP)

( * ) Notice: Subject to any disclaimer, the term of this patent is extended or adjusted under 35 U.S.C. 154(b) by 556 days.

(21) Appl. No.: 10/478,834

(22) PCT Filed: May 30, 2002

(86) PCT No.: PCT/JP02/05285

§ 371 (c)(1),
(2), (4) Date: Nov. 26, 2003

(87) PCT Pub. No.: WO02/096882

PCT Pub. Date: Dec. 5, 2002

(65) Prior Publication Data

US 2004/0116744 A1    Jun. 17, 2004

(30) Foreign Application Priority Data

May 31, 2001   (JP)   ............................. 2001-164787

(51) Int. Cl.
*A01N 43/56*   (2006.01)
*C07D 231/14*   (2006.01)

(52) U.S. Cl. ..................................... 514/406; 548/374.1

(58) Field of Classification Search .............. 548/374.1; 514/406

See application file for complete search history.

(56) References Cited

U.S. PATENT DOCUMENTS 3,405,177 A    10/1968   Jones
3,978,091 A    8/1976   Tsuchiya et al.

2001/0041814 A1    11/2001   Tohnishi et al.

FOREIGN PATENT DOCUMENTS

| EP | 0 053 011 | 6/1982 |
| EP | 0371950 | 6/1990 |
| EP | 1006102 | 6/2000 |
| WO | WO 88/05046 | 7/1988 |
| WO | WO 91/01311 | 2/1991 |
| WO | WO 00/29398 | 5/2000 |
| WO | WO 01/23356 | 4/2001 |

OTHER PUBLICATIONS

Kim et al. "Quantitative structure-activity relationship of N-substituted phenyl-5-chloro-1,3-dimethylpyrazol-4-carboxamides" Han'guk Nonghwa Hakhoechi 1992, vol. 35, Iss 5, pp. 382-388.*
Patani et al. "Bioisosterism: A Rational Approach in Drug Design" Chemical Reviews 1996, vol. 96, Iss 8, pp. 3147-3176.*

* cited by examiner

*Primary Examiner*—Rei-tsang Shiao
*Assistant Examiner*—Joseph R Kosack
(74) *Attorney, Agent, or Firm*—Paul E. White; Manelli Denison & Selter PLLC

(57) ABSTRACT

The present invention relates to a substituted anilide derivative represented by general formula (I):

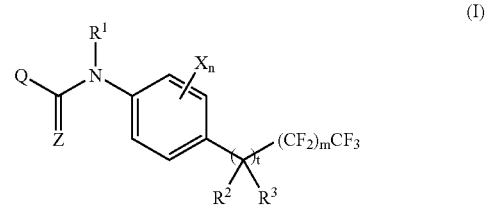

(wherein $R^1$ is a hydrogen atom, a $(C_1-C_6)$alkyl group, a halo$(C_1-C_6)$alkyl group or the like; $R^2$ is a hydrogen atom, a halogen atom or a halo$(C_1-C_6)$alkyl group; $R^3$ is a hydrogen atom, a halogen atom, a $(C_1-C_6)$alkyl group or the like; t is 0 or 1; m is an integer of 0 to 6; each of Xs is a $(C_2-C_8)$alkyl group, a $(C_1-C_8)$alkoxy group or the like in the case of t being 0, and is a halogen atom, a cyano group or the like in the case of t being 1; n is an integer of 1 to 4; Z is O or S; and Q is any of Q1 to Q25), an intermediate thereof, an agricultural and horticultural chemical, and a usage of the same.

6 Claims, No Drawings

SUBSTITUTED N-PHENYL-PHENOXY NICOTINIC ACID-(THIO)AMIDES AND THEIR USE AS HERBICIDES

This application is the national phase filing, under 35 USC 371, of international application PCT/JP02/05285 filed 30 May 2002, which designated the U.S.

TECHNICAL FIELD

The present invention relates to substituted anilide derivatives; intermediates thereof; an agricultural and horticultural chemical, in particular, an agricultural and horticultural insecticide, fungicide or acaricide, which contains said compound as an active ingredient; and a usage of the chemical.

BACKGROUND ART

JP-A-5-221994 and JP-A-10-251240 disclose that compounds analogous to the substituted anilide derivative of the present invention are useful as an agricultural and horticultural fungicide.

The production of agricultural and horticultural crops and the like is still badly damaged by insect pests and the like, and the development of a novel agricultural and horticultural chemical, in particular, agricultural and horticultural insecticide is desired because of, for example, the appearance of insect pests resistant to existing chemicals. In addition, because of the increased population of aged farmers, and the like, various labor-saving application methods are desired and the development of an agricultural and horticultural chemical having properties suitable for the application methods is desired.

DISCLOSURE OF THE INVENTION

The present inventors earnestly investigated in order to develop a novel agricultural and horticultural chemical, and consequently found that the substituted aniline derivative represented by general formula (II) of the present invention is a novel compound not known in any literature, which is a useful intermediate for the production of various derivatives having physiological activity as a medicine, an agrochemical or the like, and that a substituted anilide derivative of general formula (I) derived from said compound is a novel compound not known in any literature and is useful as an agricultural and horticultural chemical, in particular, an agricultural and horticultural insecticide, fungicide or acaricide, whereby the present invention has been accomplished.

That is, the present invention relates to a substituted anilide derivative represented by general formula (I):

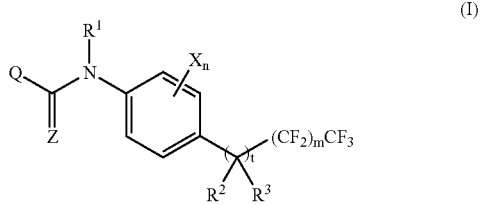

(I)

{wherein $R^1$ is a hydrogen atom, a $(C_1-C_6)$alkyl group, a halo$(C_1-C_6)$alkyl group, a $(C_1-C_6)$alkylcarbonyl group, a halo$(C_1-C_6)$alkylcarbonyl group, a phenyl group, or a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups, $R^2$ is a hydrogen atom, a halogen atom or a halo$(C_1-C_6)$alkyl group, $R^3$ is a hydrogen atom; a halogen atom; a $(C_1-C_6)$alkyl group; a halo$(C_1-C_6)$alkyl group; a cyano group; a hydroxyl group; a $(C_1-C_6)$alkoxy group; a halo$(C_1-C_6)$alkoxy group; a $(C_1-C_6)$alkoxy$(C_1-C_3)$alkoxy group; a halo$(C_1-C_6)$alkoxy$(C_1-C_3)$alkoxy group; a $(C_1-C_6)$alkylthio$(C_1-C_3)$alkoxy group; a halo$(C_1-C_6)$alkylthio$(C_1-C_3)$alkoxy group; a $(C_1-C_6)$alkylsulfinyl$(C_1-C_3)$alkoxy group; a halo$(C_1-C_6)$alkylsulfinyl$(C_1-C_3)$alkoxy group; a $(C_1-C_6)$alkylsulfonyl$(C_1-C_3)$alkoxy group; a halo$(C_1-C_6)$alkylsulfonyl $(C_1-C_3)$alkoxy group; a mono$(C_1-C_6)$alkylamino$(C_1-C_3)$alkoxy group; a di$(C_1-C_6)$alkylamino$(C_1-C_3)$alkoxy group whose $(C_1-C_6)$alkyl groups may be the same or different; a $(C_1-C_6)$alkylthio group; a halo$(C_1-C_6)$alkylthio group; a $(C_1-C_6)$alkylsulfinyl group; a halo$(C_1-C_6)$alkylsulfinyl group; a $(C_1-C_6)$alkylsulfonyl group; a halo$(C_1-C_6)$alkylsulfonyl group; an amino group; a mono$(C_1-C_6)$alkylamino group; a di$(C_1-C_6)$alkylamino group whose $(C_1-C_6)$alkyl groups may be the same or different; a phenoxy group; a substituted phenoxy group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a phenylthio group; a substituted phenylthio group having one or-more substituents which may be the same or different and are selected from halogen atoms, cyano group, nitro group, $(C_1-C_6)$alkyl groups, halo$(C_1-C_6)$alkyl groups, $(C_1-C_6)$-alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a phenylsulfinyl group; a substituted phenylsulfinyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a phenylsulfonyl group; a substituted phenylsulfonyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$ alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenyl($C_1$-$C_6$)alkoxy group; or a substituted phenyl($C_1$-$C_6$)alkoxy group having on the ring one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, t is 0 or 1, m is an integer of 0 to 6, in the case of t being 0, each of Xs, which may be the same or different, is a ($C_2$-$C_8$)alkyl group, a ($C_1$-$C_8$)alkoxy group, a ($C_1$-$C_6$)alkylthio group, a ($C_1$-$C_6$)alkylsulfinyl group, a ($C_1$-$C_6$)alkylsulfonyl group, a ($C_1$-$C_6$)alkoxy($C_1$-$C_6$)alkyl group, a mono($C_1$-$C_6$)alkylamino($C_1$-$C_6$)alkyl group, or a di($C_1$-$C_6$)alkylamino($C_1$-$C_6$)alkyl group in which the ($C_1$-$C_6$)alkyl groups of the di($C_1$-$C_6$)alkylamino group may be the same or different, and n is an integer of 1 to 4, in the case of t being 1, each of Xs, which may be the same or different, is a halogen atom; a cyano group; a ($C_1$-$C_8$)alkyl group; a halo($C_1$-$C_8$)alkyl group; a ($C_2$-$C_8$)alkenyl group; a halo($C_2$-$C_8$)alkenyl group; a ($C_2$-$C_8$)alkynyl group; a halo($C_2$-$C_8$)alkynyl group; a ($C_3$-$C_6$)cycloalkyl group; a ($C_3$-$C_6$)cycloalkyl($C_1$-$C_6$)alkyl group; a ($C_1$-$C_8$)alkoxy group; a halo($C_1$-$C_8$)alkoxy group; a ($C_1$-$C_6$)alkylthio group; a ($C_1$-$C_6$)alkylsulfinyl group; a ($C_1$-$C_6$)alkylsulfonyl group; a mono($C_1$-$C_6$)alkylamino group; a di($C_1$-$C_6$)alkylamino group whose ($C_1$-$C_6$)alkyl groups may be the same or different; a ($C_1$-$C_8$)alkylcarbonyl group; a halo($C_1$-$C_8$)alkylcarbonyl group; a ($C_1$-$C_8$)alkylthiocarbonyl group; a halo($C_1$-$C_8$)alkylthiocarbonyl group; a ($C_1$-$C_6$)alkylcarbonyl($C_1$-$C_6$)alkyl group; a halo($C_1$-$C_6$)alkylcarbonyl($C_1$-$C_6$)alkyl group; a ($C_1$-$C_6$)alkylthiocarbonyl($C_1$-$C_6$)alkyl group; a halo($C_1$-$C_6$)alkylthiocarbonyl($C_1$-$C_6$)alkyl group; a ($C_1$-$C_6$)alkoxy($C_1$-$C_6$)alkyl group; a halo($C_1$-$C_6$)alkoxy($C_1$-$C_6$)alkyl group; a ($C_1$-$C_6$)alkylthio($C_1$-$C_6$)alkyl group; a ($C_1$-$C_6$)alkylsulfinyl($C_1$-$C_6$)alkyl group; a ($C_1$-$C_6$)alkylsulfonyl($C_1$-$C_6$)alkyl group; a mono($C_1$-$C_6$)alkylamino($C_1$-$C_6$)alkyl group; a di($C_1$-$C_6$)alkylamino($C_1$-$C_6$)alkyl group in which the ($C_1$-$C_6$)alkyl groups of the di($C_1$-$C_6$)alkylamino group may be the same or different; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenoxy group; a substituted phenoxy group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenylthio group; a substituted phenylthio group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$) alkyl groups may be the same or different, and ($C_1$-$C_6$) alkoxycarbonyl groups, and n is an integer of 1 to 4, further, two adjacent Xs on the aromatic ring being able to be taken together to represent a fused ring that may have one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$) alkoxycarbonyl groups, and X being able to bind to $R^1$ to form a 5- to 8-membered ring that may contain one or two atoms which may be the same or different and are selected from oxygen atom, sulfur atom and nitrogen atom, between adjacent carbon atoms constituting the ring, Z is an oxygen atom or a sulfur atom, and Q is a substituent represented by any of the formulas Q1 to Q25:

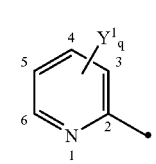

Q1

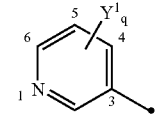

Q2

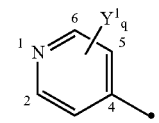

Q3

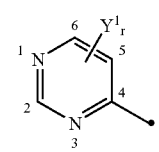

Q4

(wherein each of Y¹s, which may be the same or different, is a halogen atom; a cyano group; a nitro group; a $(C_1-C_6)$ alkyl group; a halo$(C_1-C_6)$alkyl group; a $(C_2-C_6)$alkenyl group; a halo$(C_2-C_6)$alkenyl group; a $(C_2-C_6)$alkynyl group; a halo$(C_2-C_6)$alkynyl group; a $(C_1-C_6)$alkoxy group; a halo$(C_1-C_6)$alkoxy group; a $(C_1-C_6)$alkylthio group; a halo$(C_1-C_6)$alkylthio group; a $(C_1-C_6)$alkylsulfinyl group; a halo$(C_1$-

$C_6$)alkylsulfinyl group; a ($C_1$-$C_6$)alkylsulfonyl group; a halo($C_1$-$C_6$)alkylsulfonyl group; a mono($C_1$-$C_6$)alkylamino group; a di($C_1$-$C_6$)alkylamino group whose ($C_1$-$C_6$)alkyl groups may be the same or different; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenoxy group; a substituted phenoxy group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$) alkyl groups may be the same or different, and ($C_1$-$C_6$) alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, further, two adjacent $Y^1$s on the aromatic ring being able to be taken together to represent a fused ring that may have one or more substituents which may be the same or different and are selected from halogen atoms, cyano group, nitro group, ($C_1$-$C_6$)alkyl groups, halo($C_1$-$C_6$)alkyl groups, ($C_1$-$C_6$) alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$) alkylamino groups, di($C_1$-$C_6$)alkylamino groups whose ($C_1$-$C_6$)alkyl groups may be the same or different, and ($C_1$-$C_6$) alkoxycarbonyl groups, $Y^2$ is a halogen atom; a cyano group; a nitro group; a ($C_1$-$C_6$)alkyl group; a halo($C_1$-$C_6$)alkyl group; a ($C_1$-$C_6$) alkoxy group; a halo($C_1$-$C_6$)alkoxy group; a ($C_1$-$C_6$)alkylthio group; a halo($C_1$-$C_6$)alkylthio group; a ($C_1$-$C_6$)alkylsulfinyl group; a halo($C_1$-$C_6$)alkylsulfinyl group; a ($C_1$-$C_6$)alkylsulfonyl group; a halo($C_1$-$C_6$)alkylsulfonyl group; a mono($C_1$-$C_6$)alkylamino group; a di($C_1$-$C_6$)alkylamino group whose ($C_1$-$C_6$)alkyl groups may be the same or different; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo ($C_1$-$C_6$)alkylthio groups, ($C_1$-$C_6$)alkylsulfinyl groups, halo ($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenoxy group; a substituted phenoxy group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$) alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$) alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$) alkyl groups may be the same or different, and ($C_1$-$C_6$) alkoxycarbonyl groups, $Y^3$ is a hydrogen atom, a ($C_1$-$C_6$)alkyl group, a halo($C_1$-$C_6$)alkyl group, a phenyl group, or a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$) alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$) alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, p is an integer of 0 to 2, q is an integer of 0 to 4, and r is an integer of 0 to 3)}, an agricultural and horticultural chemical, and a usage of the same. Furthermore, the present invention relates to a substituted aniline derivative represented by general formula (II):

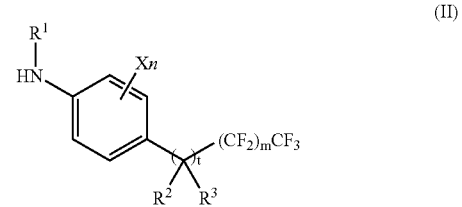

(II)

(wherein $R^1$ is a hydrogen atom, a ($C_1$-$C_6$)alkyl group, a halo($C_1$-$C_6$)alkyl group, a phenyl group, or a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, $R^2$ is a hydrogen atom, a halogen atom or a halo($C_1$-$C_6$) alkyl group, $R^3$ is a hydrogen atom; a halogen atom; a ($C_1$-$C_6$)alkyl group; a halo($C_1$-$C_6$)alkyl group; a cyano group; a hydroxyl group; a ($C_1$-$C_6$)alkoxy group; a halo($C_1$-$C_6$)alkoxy group; a ($C_1$-$C_6$)alkoxy($C_1$-$C_6$)alkoxy group; a halo($C_1$-$C_6$)alkoxy ($C_1$-$C_6$)alkoxy group; a ($C_1$-$C_6$)alkylthio($C_1$-$C_6$)alkoxy group; a halo($C_1$-$C_6$)alkylthio($C_1$-$C_6$)alkoxy group; a ($C_1$-$C_6$)alkylsulfinyl($C_1$-$C_6$)alkoxy group; a halo($C_1$-$C_6$)alkylsulfinyl($C_1$-$C_6$)alkoxy group; a ($C_1$-$C_6$)alkylsulfonyl($C_1$-$C_6$)alkoxy group; a halo($C_1$-$C_6$)alkylsulfonyl($C_1$-$C_6$)alkoxy group; a mono($C_1$-$C_6$)alkylamino($C_1$-$C_6$)alkoxy group; a di($C_1$-$C_6$)alkylamino($C_1$-$C_6$)alkoxy group whose ($C_1$-$C_6$) alkyl groups may be the same or different; a ($C_1$-$C_6$)alkylthio group; a halo($C_1$-$C_6$)alkylthio group; a ($C_1$-$C_6$)alkylsulfinyl group; a halo($C_1$-$C_6$)alkylsulfinyl group; a ($C_1$-$C_6$)alkylsulfonyl group; a halo($C_1$-$C_6$)alkylsulfonyl group; an amino group; a mono($C_1$-$C_6$)alkylamino group; a di($C_1$-$C_6$)alkylamino group whose ($C_1$-$C_6$)alkyl groups may be the same or different; a phenoxy group; a substituted phenoxy group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$) alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$) alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenylthio group; a substituted phenylthio group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$) alkyl groups may be the same or different, and ($C_1$-$C_6$) alkoxycarbonyl groups; a phenylsulfinyl group; a substituted phenylsulfinyl group having one or more substituents which may be the same or different and are selected from halogen atoms, cyano group, nitro group, ($C_1$-$C_6$)alkyl groups, halo ($C_1$-$C_6$)alkyl groups, ($C_1$-$C_6$)alkoxy groups, halo($C_1$-$C_6$) alkoxy groups, ($C_1$-$C_6$)alkylthio groups, halo($C_1$-$C_6$)alkylthio groups, ($C_1$-$C_6$)alkylsulfinyl groups, halo($C_1$-$C_6$) alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenylsulfonyl group; a substituted phenylsulfonyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$) alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$) alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenyl($C_1$-$C_6$) alkoxy group; or a substituted phenyl($C_1$-$C_6$)alkoxy group having on the ring one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, t is 1, m is an integer of 0 to 6, each of Xs, which may be the same or different, is a halogen atom, a cyano group, a ($C_1$-$C_8$)alkyl group, a halo($C_1$-$C_8$) alkyl group, a ($C_2$-$C_8$)alkenyl group, a halo($C_2$-$C_8$)alkenyl group, a ($C_2$-$C_8$)alkynyl group, a halo($C_2$-$C_8$)alkynyl group, a ($C_3$-$C_6$)cycloalkyl group, a ($C_3$-$C_6$)cycloalkyl($C_1$-$C_6$)alkyl group, a ($C_1$-$C_8$)alkoxy group, a halo($C_1$-$C_8$)alkoxy group, a ($C_1$-$C_6$)alkylthio group, a ($C_1$-$C_6$)alkylsulfinyl group, a ($C_1$-$C_6$)alkylsulfonyl group, a mono($C_1$-$C_6$)alkylamino group, a di($C_1$-$C_6$)alkylamino group whose ($C_1$-$C_6$)alkyl groups may be the same or different, a ($C_1$-$C_6$)alkylcarbonyl($C_1$-$C_6$)alkyl group, a halo($C_1$-$C_6$)alkylcarbonyl($C_1$-$C_6$)alkyl group, a ($C_1$-$C_6$)alkylthiocarbonyl($C_1$-$C_6$)alkyl group, a ($C_1$-$C_6$)alkoxy ($C_1$-$C_6$)alkyl group, a halo($C_1$-$C_6$)alkoxy($C_1$-$C_6$)alkyl group, a ($C_1$-$C_6$)alkylthio($C_1$-$C_6$)alkyl group, a ($C_1$-$C_6$)alkylsulfinyl ($C_1$-$C_6$)alkyl group, a ($C_1$-$C_6$)alkylsulfonyl($C_1$-$C_6$)alkyl group, a mono($C_1$-$C_6$)alkylamino($C_1$-$C_6$)alkyl group, a di($C_1$-$C_6$)alkylamino($C_1$-$C_6$)alkyl group in which the ($C_1$-$C_6$)alkyl groups of the di($C_1$-$C_6$)alkylamino group may be the same or different, a phenyl group, or a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, and n is an integer of 1 to 4, further, two adjacent Xs on the aromatic ring being able to be taken together to represent a fused ring that may have one or more substituents which may be the same or different and are selected from halogen atoms, cyano group, nitro group, ($C_1$-$C_6$)alkyl groups, halo($C_1$-$C_6$)alkyl groups, ($C_1$-$C_6$) alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$) alkylamino groups, di($C_1$-$C_6$)alkylamino groups whose ($C_1$-$C_6$)alkyl groups may be the same or different, and ($C_1$-$C_6$) alkoxycarbonyl groups) which is an intermediate compound for the production of a substituted anilide derivative.

MODE FOR CARRYING OUT THE INVENTION

In the definition of general formula (I) shown for the substituted anilide derivative of the present invention, the term "halogen atom" means a chlorine atom, a bromine atom, an iodine atom or a fluorine atom. In the definition, "n-" is a prefix for "normal", "s-" is a prefix for "secondary", "t-" is a prefix for "tertiary", and "i-" is a prefix for "iso". The term "($C_1$-$C_6$)alkyl" means a linear or branched alkyl group of 1 to 6 carbon atoms, such as methyl, ethyl, n-propyl, i-propyl, n-butyl, i-butyl, s-butyl, t-butyl, n-pentyl, n-hexyl or the like. The term "halo($C_1$-$C_6$)alkyl" means a substituted and linear or branched alkyl group of 1 to 6 carbon atoms having as the substituent(s) one or more halogen atoms which may be the same or different. The term "($C_3$-$C_6$)cycloalkyl" means a cyclic alkyl group of 3 to 6 carbon atoms, such as cyclopropyl, cyclobutyl, cyclopentyl, cyclohexyl or the like.

The term "heterocyclic group" means a 5- or 6-membered heterocyclic group having one or more heteroatoms selected from oxygen atom, sulfur atom and nitrogen atom. The heterocyclic group includes, for example, pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group and pyrazolyl group. The "fused ring" includes, for example, naphthalene, tetrahydronaphthalene, indene, indane, quinoline, quinazoline, indole, indoline, chroman, isochroman, benzodioxane, benzodioxole, benzofuran, dihydrobenzofuran, benzothiophene, dihydrobenzothiophene, benzoxazole, benzothiazole, benzimidazole and indazole.

The substituted anilide derivative of general formula (I) of the present invention contains one or more asymmetric centers in its structural formula in some cases and has two or more optical isomers and diastereomers in some cases. The present invention also includes all of the individual optical isomers and mixtures consisting of these isomers in any ratio. The substituted anilide derivative of general formula (I) of the present invention has two geometrical isomers due to a carbon-carbon double bond in its structural formula in some cases. The present invention also includes all of the individual geometrical isomers and mixtures consisting of these isomers in any ratio.

In the substituted anilide derivative of general formula (I) of the present invention, Q is preferably Q9, Q14 and Q15, particularly preferably Q9; $Y^1$ is preferably a halogen atom or a $(C_1\text{-}C_2)$alkyl group, particularly preferably a 3,5-dimethyl group; $Y^3$ is preferably a $(C_1\text{-}C_3)$alkyl group or a phenyl group, particularly preferably a methyl group; $X_n$ is preferably a $(C_5\text{-}C_7)$alkyl group at the 2-position, particularly preferably $C_6$alkyl group at the 2-position; Z is particularly preferably an oxygen atom; $R^1$ is particularly preferably a hydrogen atom; $R^2$ is particularly preferably a trifluoromethyl group; $R^3$ is preferably a hydrogen atom, a halogen atom or a $(C_1\text{-}C_2)$alkoxy group, particularly preferably a hydrogen atom; m is particularly preferably 0; and t is particularly preferably 1.

Typical production processes of the substituted anilide derivative represented by general formula (I) of the present invention are described below but they are not intended in any way to limit the scope of the present invention.

wherein $R^1$, $R^2$, $R^3$, X, m, n, t and Q are as defined above, $R^4$ is a hydrogen atom, a $(C_1\text{-}C_6)$alkyl group, a halo$(C_1\text{-}C_6)$alkyl group, a phenyl group, a substituted phenyl group or a phenyl $(C_1\text{-}C_4)$alkyl group, and W is —O—, —S— or —N($R^4$)— wherein $R^4$ is as defined above.

A substituted anilide derivative (I-3), i.e., a substituted anilide derivative of general formula (I) in which Z is O, can be produced by allowing an aniline derivative of any of general formula (II-1) to general formula (II-3) to react with a heterocyclic carboxylic acid chloride of general formula (III) in an inert solvent in the presence or absence of a base, or by allowing an aniline derivative of any of general formula (II-1) to general formula (II-3) to react with a heterocyclic carboxylic acid of general formula (IV) in an inert solvent in the presence of a condensing agent and in the presence or absence of a base. The production may be carried out by any conventional production process of an amide.

The aniline derivative of general formula (II-2) can be produced by reducing the aniline derivative of general formula (II-1) in an inert solvent in the presence of a reducing agent.

The aniline derivative of general formula (II-3) can be produced by allowing the aniline derivative of general formula (II-1) to react with an alcohol derivative, thiol derivative or amine derivative of general formula (V) in an inert solvent in the presence or absence of a base.

General Formula (II-1)→General Formula (II-2)

The reducing agent usable in this reaction includes, for example, metal hydrides such as aluminum lithium hydride, lithium boron hydride, sodium boron hydride, diisobutylaluminum hydride, sodium bis(2-methoxyethoxy)aluminum hydride, etc.; and metals or metal salts, such as metallic lithium, etc. As to the amount of the reducing agent used, the reducing agent may be used in an amount properly chosen in the range of 1 equivalent to excess equivalents per equivalent of the aniline derivative of general formula (II-1).

As the inert solvent used in the reaction, any inert solvent may be used so long as it does not markedly inhibit the progress of the reaction. There can be exemplified inert solvent including, for example, aromatic hydrocarbons such as benzene, toluene, xylene, etc.; halogenated hydrocarbons

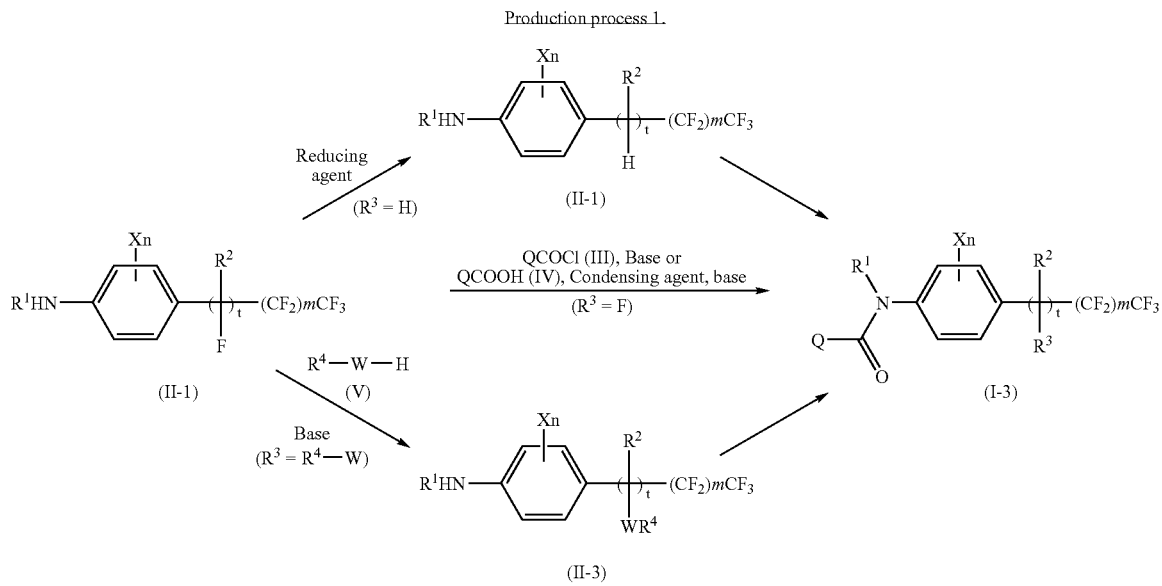

Production process 1.

such as methylene chloride, chloroform, carbon tetrachloride, etc.; halogenated aromatic hydrocarbons such as chlorobenzene, dichlorobenzene, etc.; and acyclic or cyclic ethers such as diethyl ether, dioxane, tetrahydrofuran, etc. These inert solvents may be used singly or as a mixture thereof.

As to the reaction temperature, the reaction can be carried out at room temperature to the boiling point of the inert solvent used. Although the reaction time is varied depending on the scale of reaction, the reaction temperature, etc., the reaction may be carried out for a period ranging from several minutes to 50 hours.

After completion of the reaction, the desired compound is isolated from the reaction system containing the desired compound by a conventional method, and if necessary, purified by recrystallization, column chromatography, etc., whereby the desired compound can be produced. The desired compound can be subjected to the subsequent reaction step without isolation from the reaction system.

General Formula (II-1)→General Formula (II-3)

The base usable in this reaction includes metal hydrides such as lithium hydride, sodium hydride, potassium hydride, etc.; metal alcoholates such as sodium methoxide, sodium ethoxide, potassium t-butoxide, etc.; and alkyl metals such as n-butyl-lithium, s-butyllithium, t-butyllithium, etc. As to the amount of the base used, the base may be used in an amount properly chosen in the range of 1 equivalent to excess equivalents per equivalent of the aniline derivative of general formula (II-1).

As the inert solvent used in the reaction, any inert solvent may be used so long as it does not markedly inhibit the progress of the reaction. There can be exemplified inert solvent including, for example, aromatic hydrocarbons such as benzene, toluene, xylene, etc.; alcohols such as methanol, ethanol, etc.; and acyclic or cyclic ethers such as diethyl ether, 1,2-dimethoxyethane, dioxane, tetrahydrofuran, etc. These inert solvents may be used singly or as a mixture thereof.

As to the reaction temperature, the reaction can be carried out at −70° C. to the boiling point of the inert solvent used. Although the reaction time is varied depending on the scale of reaction, the reaction temperature, etc., the reaction may be carried out for a period ranging from several minutes to 50 hours.

After completion of the reaction, the desired compound is isolated from the reaction system containing the desired compound by a conventional method, and if necessary, purified by recrystallization, column chromatography, etc., whereby the desired compound can be produced. The desired compound can be subjected to the subsequent reaction step without isolation from the reaction system.

General Formula (II-1), General Formula (II-2) or General Formula (II-3)→General Formula (I-3)

The condensing agent used in this reaction includes, for example, diethyl cyanophosphonate (DEPC), carbonyl-diimidazole (CDI), 1,3-dicyclohexylcarbodiimide (DCC), chlorocarbonic acid esters and 2-chloro-1-methylpyridinium iodide.

As the base used in the reaction, inorganic bases or organic bases are exemplified. The inorganic bases include, for example, hydroxides of alkali metal atoms, such as sodium hydroxide, potassium hydroxide, etc.; hydrides of alkali metals, such as sodium hydride, potassium hydride, etc.; alkali metal salts of alcohols, such as sodium ethoxide, potassium t-butoxide, etc.; and carbonates such as sodium carbonate, potassium carbonate, sodium hydrogencarbonate, etc. The organic bases include, for example, triethylamine, pyridine and DBU. As to the amount of the base used, the base may be used in an amount properly chosen in the range of 1 mole to excess moles per mole of the heterocyclic carboxylic acid derivative of general formula (IV).

As the inert solvent used in the reaction, any inert solvent may be used so long as it does not markedly inhibit the progress of the reaction. There can be exemplified inert solvent including aromatic hydrocarbons such as benzene, toluene, xylene, etc.; halogenated hydrocarbons such as methylene chloride, chloroform, carbon tetrachloride, etc.; halogenated aromatic hydrocarbons such as chlorobenzene, dichlorobenzene, etc.; acyclic or cyclic ethers such as diethyl ether, dioxane, tetrahydrofuran, etc.; esters such as ethyl acetate, etc.; amides such as dimethylformamide, dimethylacetamide, etc.; dimethyl sulfoxide; 1,3-dimethyl-2-imidazolidinone; acetone; methyl ethyl ketone; and the like. These inert solvents may be used singly or as a mixture thereof.

Since the reaction is an equimolar reaction, it is sufficient that the reactants are used in equimolar amounts, though either of them may be used in excess. As to the reaction temperature, the reaction can be carried out at room temperature to the boiling point of the inert solvent used. Although the reaction time is varied depending on the scale of reaction, the reaction temperature, etc., the reaction may be carried out for a period ranging from several minutes to 48 hours.

After completion of the reaction, the desired compound is isolated from the reaction system containing the desired compound by a conventional method, and if necessary, purified by recrystallization, column chromatography, etc., whereby the desired compound can be produced.

The aniline derivative of general formula (II-1), i.e., the starting material in the reaction can be produced according to the production process disclosed in JP-A-11-302233 or JP-A-2001-122836.

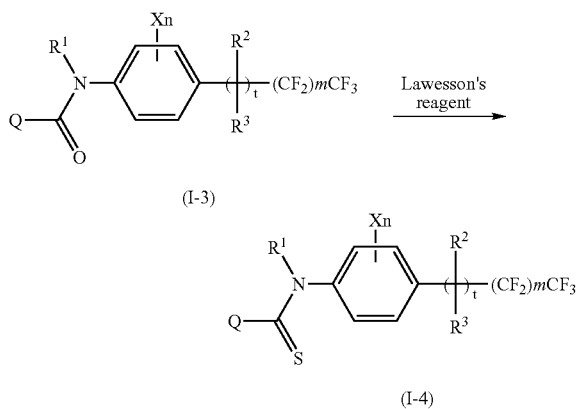

wherein $R^1$, $R^2$, $R^3$, X, m, n, t and Q are as defined above.

A substituted anilide derivative (I-4), i.e., a substituted anilide derivative of general formula (I) in which Z is S, can be produced by allowing a substituted anilide derivative of general formula (I-3) to react with Lawson reagent according to a well-known method (Tetrahedron Lett., 21 (42), 4061 (1980)).

Typical compounds as the substituted anilide derivative of general formula (I) are listed in Tables 1 to 4 and typical compounds as the substituted aniline derivative of general formula (II) are listed in Table 6, but they are not intended in any way to limit the scope of the present invention. In Tables 1 to 4 and Table 6, the physical property is melting point (° C.) or refractive index (the value in the parenthesis is temperature (° C.)), and "Me" indicates a methyl group, "Et" an ethyl group, "Pr" a propyl group, "Bu" a butyl group, and "Ph" a phenyl group.

General Formula (1)

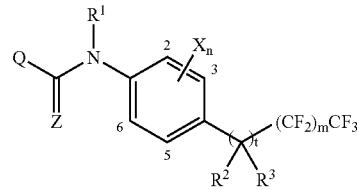

(I)

TABLE 1

($Q = Q9, R^1 = H, R^2 = CF_3, Z = O, t = 1$)

| No. | Xn | $Y^1_p$ | $Y^3$ | m | $R^3$ | Physical property |
|---|---|---|---|---|---|---|
| 1-1 | 2-Me | 3-$CF_3$ | Me | 0 | F | 146-148 |
| 1-2 | 2-Et-6-s-Bu | 3-Me-5-Cl | Me | 0 | H | 119 |
| 1-3 | 2-n-Pr | 3-$CF_3$ | Me | 0 | F | 152-153 |
| 1-4 | 2-n-Pr | 3-Me-5-Cl | Me | 0 | H | 85-87 |
| 1-5 | 2-i-Pr | 3-$CF_3$ | Me | 0 | F | 170-172 |
| 1-6 | 2-i-Bu | 3-Me-5-Cl | Me | 0 | H | |
| 1-7 | 2-i-Bu | 3-Me-5-Cl | Me | 0 | OMe | |
| 1-8 | 2-s-Bu | 3-Me-5-Cl | Me | 0 | H | 106 |
| 1-9 | 2-s-Bu | 3-Me-5-Cl | Me | 0 | OMe | |
| 1-10 | 2-t-Bu | 3-Me-5-Cl | Me | 0 | H | 124-125 |
| 1-11 | 2-t-Bu | 3-Me-5-Cl | Me | 0 | OMe | |
| 1-12 | 2-$(CH_2)_4$-3 | 3-$CF_3$ | Me | 0 | F | 125-128 |
| 1-13 | 2-$(CH_2)_4$-3 | 3-Me-5-Cl | Me | 0 | F | |
| 1-14 | 2-$(CH_2)_4$-3 | 3-Me-5-Cl | Me | 0 | H | 165-166 |
| 1-15 | 2-$(CH_2)_4$-3 | 3-Me-5-Cl | Me | 0 | OMe | |
| 1-16 | 2-CH=CH—CH=CH-3 | 3-Me-5-Cl | Me | 0 | F | |
| 1-17 | 2-CH=CH—CH=CH-3 | 3-Me-5-Cl | Me | 0 | H | 130-131 |
| 1-18 | 2-CH=CH—CH=CH-3 | 3-Me-5-Cl | Me | 0 | OMe | |
| 1-19 | 2-Ph | 3-$CF_3$ | Me | 0 | F | 139-140 |
| 1-20 | 2-Ph | 3-Me-5-Cl | Me | 0 | H | 145-147 |
| 1-21 | 2-CH(Me)$CHMe_2$ | 3-Me-5-Cl | Me | 0 | F | 121 |
| 1-22 | 2-CH(Me)$CH_2CH_2CH_3$ | 3-Me-5-Cl | Me | 0 | H | 82-83 |
| 1-23 | 2-CH(Me)$CH_2CH_2CH_3$ | 3-Me-5-Cl | Me | 0 | OMe | 1.4983(19.1) |
| 1-24 | 2-CH(Me)$CHMe_2$ | 3,5-$Me_2$ | Me | 0 | F | |
| 1-25 | 2-CH(Me)$CH_2CH_2CH_3$ | 3,5-$Me_2$ | Me | 0 | H | 1.5051(20.1) |
| 1-26 | 2-CH(Me)$CH_2CH_2CH_3$ | 3,5-$Me_2$ | Me | 0 | OMe | 1.4921(20.2) |
| 1-27 | 2-CH(Me)$CH_2CHMe_2$ | H | Me | 0 | H | |
| 1-28 | 2-CH(Me)$CH_2CHMe_2$ | 3-$CF_3$ | Me | 0 | F | 138-139 |
| 1-29 | 2-CH(Me)$CH_2CHMe_2$ | 3-$CF_3$ | Et | 0 | H | |
| 1-30 | 2-CH(Me)$CH_2CHMe_2$ | 3-$CF_3$ | Me | 0 | H | 146-147 |
| 1-31 | 2-CH(Me)$CH_2CHMe_2$ | 3-$CF_3$ | Me | 0 | OMe | |
| 1-32 | 2-CH(Me)$CH_2CHMe_2$ | 3-$CF_3$ | Me | 0 | OEt | |
| 1-33 | 2-CH(Me)$CH_2CHMe_2$ | 3-$CF_3$ | $CHF_2$ | 0 | H | 1.4650(19.9) |
| 1-34 | 2-CH(Me)$CH_2CHMe_2$ | 3-Me | Me | 0 | H | 1.4970(19.9) |
| 1-35 | 2-CH(Me)$CH_2CHMe_2$ | 3-Et | Me | 0 | H | 35-38 |
| 1-36 | 2-CH(Me)$CH_2CHMe_2$ | 3-i-Pr | Me | 0 | H | 45-47 |
| 1-37 | 2-CH(Me)$CH_2CHMe_2$ | 3-F | Me | 0 | H | |
| 1-38 | 2-CH(Me)$CH_2CHMe_2$ | 3-Cl | Me | 0 | H | |
| 1-39 | 2-CH(Me)$CH_2CHMe_2$ | 3-Br | Me | 0 | H | 1.5111(22.2) |
| 1-40 | 2-CH(Me)$CH_2CHMe_2$ | 3-I | Me | 0 | H | Amorphous |
| 1-41 | 2-CH(Me)$CH_2CHMe_2$ | 3-SMe | Me | 0 | H | 129-130 |
| 1-42 | 2-CH(Me)$CH_2CHMe_2$ | 3-SOMe | Me | 0 | H | |
| 1-43 | 2-CH(Me)$CH_2CHMe_2$ | 3-$SO_2$Me | Me | 0 | H | |
| 1-44 | 2-CH(Me)$CH_2CHMe_2$ | 3-OMe | Me | 0 | H | 102-105 |
| 1-45 | 2-CH(Me)$CH_2CHMe_2$ | 5-Me | Me | 0 | H | 1.4790(25.2) |
| 1-46 | 2-CH(Me)$CH_2CHMe_2$ | 5-SMe | Me | 0 | H | 1.6201(16.8) |
| 1-47 | 2-CH(Me)$CH_2CHMe_2$ | 5-SOMe | Me | 0 | H | 1.4930(23.7) |
| 1-48 | 2-CH(Me)$CH_2CHMe_2$ | 5-$SO_2$Me | Me | 0 | H | 48 |
| 1-49 | 2-CH(Me)$CH_2CHMe_2$ | 5-F | Me | 0 | H | |
| 1-50 | 2-CH(Me)$CH_2CHMe_2$ | 5-Cl | Me | 0 | H | |
| 1-51 | 2-CH(Me)$CH_2CHMe_2$ | 5-Cl | Et | 0 | H | 1.5110(21.7) |
| 1-52 | 2-CH(Me)$CH_2CHMe_2$ | 5-Cl | $CH_2CH_2F$ | 0 | H | 1.4931(22.5) |
| 1-53 | 2-CH(Me)$CH_2CHMe_2$ | 5-Br | Me | 0 | H | |
| 1-54 | 2-CH(Me)$CH_2CHMe_2$ | 5-Br | Et | 0 | H | 1.5061 |
| 1-55 | 2-CH(Me)$CH_2CHMe_2$ | 5-Br | t-Bu | 0 | H | 67-68 |
| 1-56 | 2-CH(Me)$CH_2CHMe_2$ | 5-I | Me | 0 | H | 119-120 |
| 1-57 | 2-CH(Me)$CH_2CHMe_2$ | 5-I | Et | 0 | H | 132-133 |
| 1-58 | 2-CH(Me)$CH_2CHMe_2$ | 5-I | t-Bu | 0 | H | 98-99 |
| 1-59 | 2-CH(Me)$CH_2CHMe_2$ | 5-I | Ph | 0 | H | 127-128 |
| 1-60 | 2-CH(Me)$CH_2CHMe_2$ | 3-Cl-5-Me | Me | 0 | H | 95-97 |

TABLE 1-continued (Q = Q9, R$^1$ = H, R$^2$ = CF$_3$, Z = O, t = 1)

| No. | Xn | Y$^1_p$ | Y$^3$ | m | R$^3$ | Physical property |
|---|---|---|---|---|---|---|
| 1-61 | 2-CH(Me)CH$_2$CHMe$_2$ | 3-Br-5-Me | Me | 0 | H | 1.5208(21.1) |
| 1-62 | 2-CH(Me)CH$_2$CHMe$_2$ | 3-I-5-Me | Me | 0 | H | 1.5252(21.1) |
| 1-63 | 2-CH(Me)CH$_2$CHMe$_2$ | 3-I-5-Me | Et | 0 | H | 170-171 |
| 1-64 | 2-CH(Me)CH$_2$CHMe$_2$ | 3-Me-5-F | Me | 0 | F | |
| 1-65 | 2-CH(Me)CH$_2$CHMe$_2$ | 3-Me-5-F | Me | 0 | H | 1.4974(22.8) |
| 1-66 | 2-CH(Me)CH$_2$CHMe$_2$ | 3-Me-5-F | Me | 0 | OMe | |
| 1-67 | 2-CH(Me)CH$_2$CHMe$_2$ | 3-Me-5-F | Me | 1 | F | |
| 1-68 | 2-CH(Me)CH$_2$CHMe$_2$ | 3-Me-5-F | Me | 1 | H | |
| 1-69 | 2-CH(Me)CH$_2$CHMe$_2$ | 3-Me-5-F | Me | 1 | OMe | |
| 1-70 | 2-CH(Me)CH$_2$CHMe$_2$ | 3-Me-5-Cl | Me | 0 | F | 88-90 |
| 1-71 | 2-CH(Me)CH$_2$CHMe$_2$ | 3-Me-5-Cl | Me | 0 | H | 1.5025(23.7) |
| 1-72 | 2-CH(Me)CH$_2$CHMe$_2$ | 3-Me-5-Cl | Me | 0 | OMe | Amorphous |
| 1-73 | 2-CH(Me)CH$_2$CHMe$_2$ | 3-Me-5-Cl | Me | 0 | OEt | 1.5003(15.7) |
| 1-74 | 2-CH(Me)CH$_2$CHMe$_2$ | 3-Me-5-Cl | Me | 1 | F | |
| 1-75 | 2-CH(Me)CH$_2$CHMe$_2$ | 3-Me-5-Cl | Me | 1 | H | |
| 1-76 | 2-CH(Me)CH$_2$CHMe$_2$ | 3-Me-5-Cl | Me | 1 | OMe | |
| 1-77 | 2-CH(Me)CH$_2$CHMe$_2$ | 3-Me-5-Cl | Me | 1 | OEt | |
| 1-78 | 2-CH(Me)CH$_2$CHMe$_2$ | 3-Me-5-Cl | Et | 0 | H | 1.4905(21.2) |
| 1-79 | 2-CH(Me)CH$_2$CHMe$_2$ | 3-Me-5-Cl | Et | 0 | OMe | |
| 1-80 | 2-CH(Me)CH$_2$CHMe$_2$ | 3-Me-5-Cl | Et | 0 | OEt | |
| 1-81 | 2-CH(Me)CH$_2$CHMe$_2$ | 3-Me-5-Br | Me | 0 | H | 134-135 |
| 1-82 | 2-CH(Me)CH$_2$CHMe$_2$ | 3-Me-5-Br | Me | 0 | OMe | 96-97 |
| 1-83 | 2-CH(Me)CH$_2$CHMe$_2$ | 3-Me-5-Br | Et | 0 | OH | 1.5140(22.2) |
| 1-84 | 2-CH(Me)CH$_2$CHMe$_2$ | 3-Me-5-Br | Et | 0 | H | 153-155 |
| 1-85 | 2-CH(Me)CH$_2$CHMe$_2$ | 3-Et-5-Br | Me | 0 | H | 110-112 |
| 1-86 | 2-CH(Me)CH$_2$CHMe$_2$ | 3-Et-5-Br | Me | 0 | OMe | Amorphous |
| 1-87 | 2-CH(Me)CH$_2$CHMe$_2$ | 3-Me-5-I | Me | 0 | H | 184-185 |
| 1-88 | 2-CH(Me)CH$_2$CHMe$_2$ | 3-Me-5-I | Me | 0 | OMe | |
| 1-89 | 2-CH(Me)CH$_2$CHMe$_2$ | 3-Me-5-I | Et | 0 | H | 174 |
| 1-90 | 2-CH(Me)CH$_2$CHMe$_2$ | 3-Me-5-SMe | Me | 0 | H | 1.5140(22.2) |
| 1-91 | 2-CH(Me)CH$_2$CHMe$_2$ | 3-Me-5-SMe | Me | 0 | OMe | |
| 1-92 | 2-CH(Me)CH$_2$CHMe$_2$ | 3-Me-5-SOMe | Me | 0 | H | 42-43 |
| 1-93 | 2-CH(Me)CH$_2$CHMe$_2$ | 3-Me-5-SOMe | Me | 0 | OMe | |
| 1-94 | 2-CH(Me)CH$_2$CHMe$_2$ | 3-Me-5-SO$_2$Me | Me | 0 | H | 1.4993(22.1) |
| 1-95 | 2-CH(Me)CH$_2$CHMe$_2$ | 3-Me-5-SO$_2$Me | Me | 0 | OMe | |
| 1-96 | 2-CH(Me)CH$_2$CHMe$_2$ | 3-Me-5-OMe | Me | 0 | H | 1.5020(20.9) |
| 1-97 | 2-CH(Me)CH$_2$CHMe$_2$ | 3-Me-5-OMe | Me | 0 | OMe | |
| 1-98 | 2-CH(Me)CH$_2$CHMe$_2$ | 3-Me-5-OPh | Me | 0 | H | 1.5182(20.5) |
| 1-99 | 2-CH(Me)CH$_2$CHMe$_2$ | 3-Me-5-OPh | Me | 0 | OMe | |
| 1-100 | 2-CH(Me)CH$_2$CHMe$_2$ | 3-OMe-5-Br | Me | 0 | H | 143-144 |
| 1-101 | 2-CH(Me)CH$_2$CHMe$_2$ | 3-OMe-5-SPr-n | Me | 0 | H | 102 |
| 1-102 | 2-CH(Me)CH$_2$CHMe$_2$ | 3-CF$_3$-5-Cl | Et | 0 | H | |
| 1-103 | 2-CH(Me)CH$_2$CHMe$_2$ | 3-CF$_3$-5-Cl | Me | 0 | H | 102-104 |
| 1-104 | 2-CH(Me)CH$_2$CHMe$_2$ | 3-CF$_3$-5-Cl | Me | 0 | OMe | 1.4712(18.2) |
| 1-105 | 2-CH(Me)CH$_2$CHMe$_2$ | 3-CF$_3$-5-OPh | Me | 0 | H | 1.4951(19.4) |
| 1-106 | 2-CH(Me)CH$_2$CHMe$_2$ | 3,5-Me$_2$ | Me | 0 | F | 81-82 |
| 1-107 | 2-CH(Me)CH$_2$CHMe$_2$ | 3,5-Me$_2$ | Me | 0 | H | 1.4958(15.7) |
| 1-108 | 2-CH(Me)CH$_2$CHMe$_2$ | 3,5-Me$_2$ | Me | 0 | OMe | 94-96 |
| 1-109 | 2-CH(Me)CH$_2$CHMe$_2$ | 3,5-Me$_2$ | Me | 0 | OEt | 1.4958(20.1) |
| 1-110 | 2-CH(Me)CH$_2$CHMe$_2$ | 3,5-Me$_2$ | Me | 1 | F | |
| 1-111 | 2-CH(Me)CH$_2$CHMe$_2$ | 3,5-Me$_2$ | Me | 1 | H | |
| 1-112 | 2-CH(Me)CH$_2$CHMe$_2$ | 3,5-Me$_2$ | Me | 1 | OMe | |
| 1-113 | 2-CH(Me)CH$_2$CHMe$_2$ | 3,5-Me$_2$ | Me | 1 | OEt | |
| 1-114 | 2-CH(Me)CH$_2$CHMe$_2$ | 3,5-Me$_2$ | Et | 0 | F | 1.4950(18.4) |
| 1-115 | 2-CH(Me)CH$_2$CHMe$_2$ | 3,5-Me$_2$ | Et | 0 | H | |
| 1-116 | 2-CH(Me)CH$_2$CHMe$_2$ | 3,5-Me$_2$ | Et | 0 | OMe | |
| 1-117 | 2-CH(Me)CH$_2$CHMe$_2$ | 3,5-Me$_2$ | Et | 0 | OEt | |
| 1-118 | 2-CH(Me)CH$_2$CHMe$_2$ | 3,5-Me$_2$ | n-Pr | 0 | F | 1.4907(19.2) |
| 1-119 | 2-CH(Me)CH$_2$CHMe$_2$ | 3,5-Me$_2$ | n-Pr | 0 | H | 1.4970(17.4) |
| 1-120 | 2-CH(Me)CH$_2$CHMe$_2$ | 3,5-Me$_2$ | n-Pr | 0 | OMe | |
| 1-121 | 2-CH(Me)CH$_2$CHMe$_2$ | 3,5-Me$_2$ | n-Pr | 0 | OEt | |
| 1-122 | 2-CH(Me)CH$_2$CHMe$_2$ | 3,5-Me$_2$ | Ph | 0 | F | |
| 1-123 | 2-CH(Me)CH$_2$CHMe$_2$ | 3,5-Me$_2$ | Ph | 0 | H | |
| 1-124 | 2-CH(Me)CH$_2$CHMe$_2$ | 3,5-Me$_2$ | Ph | 0 | OMe | |
| 1-125 | 2-CH(Me)CH$_2$CHMe$_2$ | 3,5-Me$_2$ | Ph | 0 | OEt | |
| 1-126 | 2-CH(Me)CH$_2$CHMe$_2$ | 3,5-F$_2$ | Me | 0 | F | |
| 1-127 | 2-CH(Me)CH$_2$CHMe$_2$ | 3,5-F$_2$ | Me | 0 | H | |
| 1-128 | 2-CH(Me)CH$_2$CHMe$_2$ | 3,5-F$_2$ | Me | 0 | OMe | |
| 1-129 | 2-CH(Me)CH$_2$CHMe$_2$ | 3,5-Cl$_2$ | Me | 0 | H | 73 |
| 1-130 | 2-CH(Me)CH$_2$CHMe$_2$ | 3,5-Cl$_2$ | Me | 0 | OMe | |
| 1-131 | 2-CH(Me)CH$_2$CHMe$_2$ | 3,5-Cl$_2$ | Et | 0 | H | 129-130 |
| 1-132 | 2-CH(Me)CH$_2$CHMe$_2$ | 3-Et-5-Cl | Me | 0 | H | Amorphous |
| 1-133 | 2-CH(Me)CH$_2$CHMe$_2$ | 3-n-Pr-5-Cl | Me | 0 | H | 1.4890(21.5) |
| 1-134 | 2-CH(Me)CH$_2$CHMe$_2$ | 3-i-Pr-5-Cl | Me | 0 | H | 1.4822(20.3) |

TABLE 1-continued (Q = Q9, R$^1$ = H, R$^2$ = CF$_3$, Z = O, t = 1)

| No. | Xn | Y$^1$$_p$ | Y$^3$ | m | R$^3$ | Physical property |
|---|---|---|---|---|---|---|
| 1-135 | 2-CH(Me)CH$_2$CHMe$_2$ | 3-t-Bu-5-Cl | Me | 0 | H | 1.4881(20.3) |
| 1-136 | 2-CH(Me)CH$_2$CMe$_2$-3 | 3-Me-5-Cl | Me | 0 | F | |
| 1-137 | 2-CH(Me)CH$_2$CMe$_2$-3 | 3-Me-5-Cl | Me | 0 | H | |
| 1-138 | 2-CH(Me)CH$_2$CMe$_2$-3 | 3-Me-5-Cl | Me | 0 | OMe | |
| 1-139 | 2-CH(Me)CH$_2$CMe$_2$-3 | 3-Me-5-Cl | Me | 1 | F | |
| 1-140 | 2-CH(Me)CH$_2$CMe$_2$-3 | 3-Me-5-Cl | Me | 1 | H | |
| 1-141 | 2-CH(Me)CH$_2$CMe$_2$-3 | 3-Me-5-Cl | Me | 1 | OMe | |
| 1-142 | 2-CH(Me)(CH$_2$)$_3$Me | 3-Me-5-Cl | Me | 0 | F | 1.4931(19.5) |
| 1-143 | 2-CH(Me)(CH$_2$)$_3$Me | 3-Me-5-Cl | Me | 0 | H | 1.5020(19.5) |
| 1-144 | 2-CH(Me)(CH$_2$)$_3$Me | 3-Me-5-Cl | Me | 0 | OMe | 1.5003(19.6) |
| 1-145 | 2-CH(Me)(CH$_2$)$_2$CH Me$_2$ | 3-Me-5-Cl | Me | 0 | F | 1.4907(20.3) |
| 1-146 | 2-CH(Me)(CH$_2$)$_2$CH Me$_2$ | 3-Me-5-Cl | Me | 0 | H | 1.4905(20.4) |
| 1-147 | 2-CH(Me)(CH$_2$)$_2$CH Me$_2$ | 3-Me-5-Cl | Me | 0 | OMe | |
| 1-148 | 2-CH(Me)(CH$_2$)$_2$CH Me$_2$ | 3,5-Me$_2$ | Me | 0 | F | Amorphous |
| 1-149 | 2-CH(Me)(CH$_2$)$_2$CH Me$_2$ | 3,5-Me$_2$ | Me | 0 | H | |
| 1-150 | 2-CH(Me)(CH$_2$)$_2$CH Me$_2$ | 3,5-Me$_2$ | Me | 0 | OMe | |
| 1-151 | 2-CH(Me)CH$_2$CHMe$_2$-3-Me | 3,5-Me$_2$ | Me | 0 | F | 1.4904(25.5) |
| 1-152 | 2-CH(Me)CH$_2$CHMe$_2$-3-Me | 3,5-Me$_2$ | Me | 0 | H | 1.4863(25.5) |
| 1-153 | 2-CH(Me)CH$_2$CH(Me)CH$_2$CH$_3$ | 3-Me-5-Cl | Me | 0 | OMe | |
| 1-154 | 2-C(Me)=CHCHMe$_2$-3-Me | 3,5-Me$_2$ | Me | 0 | F | 1.4950(25.5) |
| 1-155 | 2-C(Me)=CHCHMe$_2$-3-Me | 3,5-Me$_2$ | Me | 0 | H | 1.5052(25.2) |
| 1-156 | 2-CH(Me)CH$_2$CH(Me)CH$_2$CH$_3$ | 3,5-Me$_2$ | Me | 0 | OMe | |
| 1-157 | 2-CH(Me)Ph | 3,5-Me$_2$ | Me | 0 | F | |
| 1-158 | 2-CH(Me)Ph | 3,5-Me$_2$ | Me | 0 | H | |
| 1-159 | 2-CH(Me)Ph | 3,5-Me$_2$ | Me | 0 | OMe | |
| 1-160 | 2-CH(Me)CH$_2$CMe$_3$ | 3,5-Me$_2$ | Me | 0 | F | |
| 1-161 | 2-CH(Me)CH$_2$CMe$_3$ | 3,5-Me$_2$ | Me | 0 | H | |
| 1-162 | 2-CH(Me)CH$_2$CMe$_3$ | 3,5-Me$_2$ | Me | 0 | OMe | |
| 1-163 | 2,3-Me$_2$ | 3,5-Me$_2$ | Me | 0 | F | 132-136 |
| 1-164 | 2,3-Me$_2$ | 3,5-Me$_2$ | Me | 0 | H | 167-170 |

TABLE 2

(Q = Q9, R$^1$ = H, Z = O, t = 1)

| No. | Xn | Y$^1$$_p$ | Y$^3$ | m | R$^2$ | R$^3$ | Physical property |
|---|---|---|---|---|---|---|---|
| 2-1 | 2-CH(Me)CH$_2$CHMe$_2$ | 3,5-Me$_2$ | Me | 0 | F | F | |
| 2-2 | 2-CH(Me)CH$_2$CHMe$_2$ | 3,5-Me$_2$ | Me | 0 | H | H | |
| 2-3 | 2-CH(Me)CH$_2$CHMe$_2$ | 3,5-Me$_2$ | Me | 2 | F | F | |
| 2-4 | 2-CH(Me)CH$_2$CHMe$_2$ | 3,5-Me$_2$ | Me | 2 | H | H | |
| 2-5 | 2-CH(Me)CH$_2$CHMe$_2$ | 3,5-Me$_2$ | Me | 4 | F | F | |
| 2-6 | 2-CH(Me)CH$_2$CHMe$_2$ | 3,5-Me$_2$ | Me | 4 | H | H | |
| 2-7 | 2-CH(Me)CH$_2$CHMe$_2$ | 3,5-Me$_2$ | Me | 6 | F | F | |
| 2-8 | 2-CH(Me)CH$_2$CHMe$_2$ | 3,5-Me$_2$ | Me | 6 | H | H | |
| 2-9 | 2-CH(Me)CH$_2$CHMe$_2$ | 3-Me-5-Cl | Me | 0 | F | F | |
| 2-10 | 2-CH(Me)CH$_2$CHMe$_2$ | 3-Me-5-Cl | Me | 0 | H | H | |
| 2-11 | 2-CH(Me)CH$_2$CHMe$_2$ | 3-Me-5-Cl | Me | 2 | F | F | |
| 2-12 | 2-CH(Me)CH$_2$CHMe$_2$ | 3-Me-5-Cl | Me | 2 | H | H | |
| 2-13 | 2-CH(Me)CH$_2$CHMe$_2$ | 3-Me-5-Cl | Me | 4 | F | F | |
| 2-14 | 2-CR(Me)CH$_2$CHMe$_2$ | 3-Me-5-Cl | Me | 4 | H | H | |
| 2-15 | 2-CH(Me)CH$_2$CHMe$_2$ | 3-Me-5-Cl | Me | 6 | F | F | |
| 2-16 | 2-CH(Me)CH$_2$CHMe$_2$ | 3-Me-5-Cl | Me | 6 | H | H | |

TABLE 3

(R$^1$ = H, R$^2$ = CF$_3$, Z = O, m = 0, t = 1)

| No. | Q | Xn | Y$^1$$_{p,q,r}$ or Y$^2$ | R$^3$ | Physical property |
|---|---|---|---|---|---|
| 3-1 | Q1 | 2-CH(Me)CH$_2$CHMe$_2$ | 3-CF$_3$ | H | |
| 3-2 | Q1 | 2-CH(Me)CH$_2$CHMe$_2$ | 3,5-Cl$_2$ | H | 108-109 |
| 3-3 | Q2 | 2-CH(Me)CH$_2$CHMe$_2$ | 4-CF$_3$ | H | 1.4860 (22.7) |
| 3-4 | Q2 | 2-CH(Me)CH$_2$CHMe$_2$ | 2-Cl | H | 68 |
| 3-5 | Q2 | 2-CH(Me)CH$_2$CHMe$_2$ | 2-Cl-6-Me | H | Amorphous |
| 3-6 | Q3 | 2-CH(Me)CH$_2$CHMe$_2$ | 3-CF$_3$ | H | |
| 3-7 | Q3 | 2-CH(Me)CH$_2$CHMe$_2$ | 2,6-Cl$_2$ | H | 1.5182 (20.5) |
| 3-8 | Q6 | 2-CH(Me)CH$_2$CHMe$_2$ | 2-SMe-4-CF$_3$ | H | |
| 3-9 | Q6 | 2-CH(Me)CH$_2$CHMe$_2$ | 4-CF$_3$ | H | |
| 3-10 | Q11 | 2-CH(Me)CH$_2$CHMe$_2$ | Me | F | 104 |
| 3-11 | Q11 | 2-CH(Me)CH$_2$CHMe$_2$ | Me | H | Amorphous |
| 3-12 | Q11 | 2-CH(Me)CH$_2$CHMe$_2$ | CF$_3$ | H | 85-88 |
| 3-13 | Q12 | 2-CH(Me)CH$_2$CHMe$_2$ | 2,4-Me$_2$ | H | 72-73 |
| 3-14 | Q12 | 2-CH(Me)CH$_2$CHMe$_2$ | 2,4-Me$_2$ | OMe | |
| 3-15 | Q13 | 2-CH(Me)CH$_2$CHMe$_2$ | 3-Br | F | |
| 3-16 | Q13 | 2-CH(Me)CH$_2$CHMe$_2$ | 3-Br | H | |
| 3-17 | Q13 | 2-CH(Me)CH$_2$CHMe$_2$ | 3-Br | OMe | |
| 3-18 | Q14 | 2-CH(Me)CH$_2$CHMe$_2$ | 2-Br | H | |
| 3-19 | Q14 | 2-CH(Me)CH$_2$CHMe$_2$ | 2-Br | OMe | |
| 3-20 | Q14 | 2-CH(Me)CH$_2$CHMe$_2$ | 2-Br | OEt | |
| 3-21 | Q14 | 2-CH(Me)CH$_2$CHMe$_2$ | 4-Br | H | 1.5080 (20.4) |
| 3-22 | Q14 | 2-CH(Me)CH$_2$CHMe$_2$ | 4-Br | OMe | |
| 3-23 | Q14 | 2-CH(Me)CH$_2$CHMe$_2$ | 4-Br | OEt | |
| 3-24 | Q14 | 2-CH(Me)CH$_2$CHMe$_2$ | 2,4-Me$_2$ | H | |
| 3-25 | Q14 | 2-CH(Me)CH$_2$CHMe$_2$ | 2,4-Me$_2$ | OMe | |
| 3-26 | Q14 | 2-CH(Me)CH$_2$CHMe$_2$ | 2,4-Me$_2$ | OEt | |
| 3-27 | Q15 | 2-CH(Me)CH$_2$CHMe$_2$ | H | H | 133.5-135 |
| 3-28 | Q15 | 2-CH(Me)CH$_2$CHMe$_2$ | 3-Cl | H | |
| 3-29 | Q15 | 2-CH(Me)CH$_2$CHMe$_2$ | 3-Br | H | |
| 3-30 | Q15 | 2-CH(Me)CH$_2$CHMe$_2$ | 3-I | H | 1.5365 (18.4) |
| 3-31 | Q15 | 2-CH(Me)CH$_2$CHMe$_2$ | 3-I | OMe | 1.5081 (18.5) |
| 3-32 | Q18 | 2-CH(Me)CH$_2$CHMe$_2$ | 2-Cl | H | 104.5-106 |

TABLE 3-continued ($R^1$ = H, $R^2$ = $CF_3$, Z = O, m = 0, t = 1)

| No. | Q | Xn | $Y^1_{p,q,r}$ or $Y^2$ | $R^3$ | Physical property |
|---|---|---|---|---|---|
| 3-33 | Q18 | 2-CH(Me)CH$_2$CHMe$_2$ | 2-Me-5-(2-Cl—Ph) | H | 1.5425 (21.1) |
| 3-34 | Q21 | 2-CH(Me)CH$_2$CHMe$_2$ | 3,5-Me$_2$ | H | Amorphous |
| 3-35 | Q21 | 2-CH(Me)CH$_2$CHMe$_2$ | 3,5-Me$_2$ | OMe | 1.4870 (19.4) |
| 3-36 | Q24 | 2-CH(Me)CH$_2$CHMe$_2$ | 3,5-Me$_2$ | H | |
| 3-37 | Q24 | 2-CH(Me)CH$_2$CHMe$_2$ | 3,5-Me$_2$ | OMe | |

TABLE 4

($R^1$ = H, $R^2$ = $CF_3$, Z = O, m = 0, t = 1)

| No. | Q | Xn | $Y^1_p$ or $_r$ | $Y^3$ | $R^3$ | Physical property |
|---|---|---|---|---|---|---|
| 4-1 | Q8 | 2-CH(Me)CH$_2$CHMe$_2$ | 4-Cl-5-Me | Me | H | 160 |
| 4-2 | Q8 | 2-CH(Me)CH$_2$CHMe$_2$ | 4-Br-5-Me | Me | H | 149-150 |
| 4-3 | Q10 | 2-CH(Me)CH$_2$CHMe$_2$ | 3-Me | Me | H | 1.4848(23.6) |
| 4-4 | Q10 | 2-CH(Me)CH$_2$CHMe$_2$ | 3-Me-4-Cl | Me | H | 108-109 |
| 4-5 | Q10 | 2-CH(Me)CH$_2$CHMe$_2$ | 3-Me-4-Br | Me | H | 112-113 |
| 4-6 | Q10 | 2-CH(Me)CH$_2$CHMe$_2$ | 3-t-Bu-4-Cl | Me | H | 1.4915(23.9) |
| 4-7 | Q10 | 2-CH(Me)CH$_2$CHMe$_2$ | 3-Me-4-NO$_2$ | Me | H | 1.4971(25.3) |
| 4-8 | Q16 | 2-CH(Me)CH$_2$CHMe$_2$ | 2,4-Me$_2$ | Me | F | |
| 4-9 | Q16 | 2-CH(Me)CH$_2$CHMe$_2$ | 2,4-Me$_2$ | Me | H | 1.5062(18.4) |
| 4-10 | Q16 | 2-CH(Me)CH$_2$CHMe$_2$ | 2,4-Me$_2$ | Me | OMe | |
| 4-11 | Q16 | 2-CH(Me)CH$_2$CHMe$_2$ | 2,4-Me$_2$ | Me | OEt | |
| 4-12 | Q16 | 2-CH(Me)CH$_2$CHMe$_2$ | 2,4-Me$_2$ | Et | F | |
| 4-13 | Q16 | 2-CH(Me)CH$_2$CHMe$_2$ | 2,4-Me$_2$ | Et | H | |
| 4-14 | Q16 | 2-CH(Me)CH$_2$CHMe$_2$ | 2,4-Me$_2$ | Et | OMe | |
| 4-15 | Q16 | 2-CH(Me)CH$_2$CHMe$_2$ | 2,4-Me$_2$ | Et | OEt | |
| 4-16 | Q17 | 2-CH(Me)CH$_2$CHMe$_2$ | 3-Me | Me | F | |
| 4-17 | Q17 | 2-CH(Me)CH$_2$CHMe$_2$ | 3-Me | Me | H | |
| 4-18 | Q17 | 2-CH(Me)CH$_2$CHMe$_2$ | 3-Me | Me | OMe | |
| 4-19 | Q17 | 2-CH(Me)CH$_2$CHMe$_2$ | 3-Me | Me | OEt | |
| 4-20 | Q17 | 2-CH(Me)CH$_2$CHMe$_2$ | 3-Cl | Et | F | |
| 4-21 | Q17 | 2-CH(Me)CH$_2$CHMe$_2$ | 3-Cl | Et | H | |
| 4-22 | Q17 | 2-CH(Me)CH$_2$CHMe$_2$ | 3-Cl | Et | OMe | |
| 4-23 | Q17 | 2-CH(Me)CH$_2$CHMe$_2$ | 3-Cl | Et | OEt | |

Table 5 shows $^1$H-NMR data of compounds having a physical property expressed by the word "amorphous" in Table 1 to 4.

TABLE 5

| No. | $^1$H-NMR[CDCl$_3$/TMS, δ value (ppm)] |
|---|---|
| 1-40 | 8.20(s, 1H), 7.98(s, 1H), 7.90(d, 1H), 7.32-7.25(m, 2H), 4.05(m, 1H), 3.96(s, 3H), 3.20(m, 1H), 1.65-1.40(m, 3H), 1.24(d, 3H), 0.84(m, 6H) |
| 1-72 | 8.04(d, 1H), 7.87(s, 1H), 7.46-7.39(m, 2H), 3.86(s, 3H), 3.47(s, 3H), 3.03(m, 3H), 2.52(s, 3H), 1.69-1.40(m, 3H), 1.23(d, 3H), 0.84(d, 6H) |
| 1-86 | 8.01(d, 1H), 7.83(s, 1H), 7.47-7.39(m, 2H), 3.91(s, 3H), 3.47(s, 3H), 3.07(m, 1H), 2.94(m, 1H), 1.67-1.40(m, 3H), 1.30-1.20(m, 6H), 0.84(d, 6H) |
| 1-132 | 7.98(d, 1H), 7.83(s, 1H), 7.30-7.21(m, 2H), 4.04(m, 1H), 3.87(s, 3H), 3.10-2.80(m, 3H), 1.63-1.40(m, 3H), 1.33-1.18(m, 6H), 0.84(d, 6H) |
| 1-148 | 8.13(d, 1H), 7.50-7.40(m, 2H), 7.33(s, 1H), 3.77(s, 3H), 2.82(m, 1H), 2.54(s, 3H), 2.51(s, 3H), 1.72-1.52(m, 2H), 1.52-1.39(m, 1H), 1.27(d, 3H), 1.21-1.10(m, 1H), 1.10-0.91(m, 1H), 0.82(d, 6H) |
| 3-5 | 8.32(s, 1H), 8.20(d, 1H), 8.01(d, 1H), 7.35-7.20(m, 3H), 4.06(m, 1H), 3.05(m, 1H), 2.61(s, 3H), 1.60-1.40(m, 3H), 1.22(d, 3H), 0.84(d, 6H) |
| 3-34 | 7.85(d, 1H), 7.31-7.20(m, 3H), 4.06(m, 1H), 2.92(m, 1H), 2.67(s, 3H), 2.51(s, 3H), 1.60-1.40(m, 3H), 1.22(t, 3H), 0.85(m, 6H) |

General Formula (II)

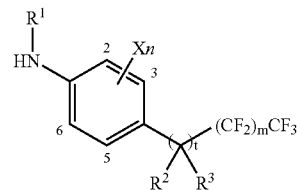

(II)

TABLE 6

($R^1$ = H, t = 1)

| No. | Xn | m | $R^2$ | $R^3$ | $^1$H-NMR[CDCl$_3$/TMS, δ value(ppm)] |
|---|---|---|---|---|---|
| 5-1 | 2-n-Pr | 0 | CF$_3$ | H | 7.12-7.02(m, 2H), 6.69(d, 1H), 4.0-3.7 (m, 3H), 2.52(q, 2H), 1.27(t, 3H) |
| 5-2 | 2-t-Bu | 0 | CF$_3$ | H | 7.17(s, 1H), 7.06(d, 1H), 6.64(d, 1H), 4.1-3.9(br, 2H), 3.91(m, 1H), 1.41(s, 9H) |
| 5-3 | 2-Ph | 0 | CF$_3$ | H | 7.52-7.32(m, 5H), 7.19-7.10(m, 2H), 6.77(d, 1H), 4.08-3.85(m, 3H) |
| 5-4 | 2-CH(Me)CHMe$_2$ | 0 | CF$_3$ | H | 7.08-7.01(m, 2H), 6.71(s, 1H), 3.91(m, 1H), 2.50(m, 1H), 1.87(m, 1H), 1.21(d, 3H), 0.92(d, 3H), 0.87(d, 3H) |
| 5-5 | 2-CH(Me)CHMe$_2$-6-Et | 0 | CF$_3$ | H | 6.96(d, 2H), 3.92(m, 1H), 3.85-3.70(br, 2H), 2.65(m, 1H), 2.53(dd, 2H), 1.80-1.50(m, 2H), 1.23(d, 3H), 0.90(t, 3H) |
| 5-6 | 2-(CH$_2$)$_4$-3 | 0 | CF$_3$ | H | 7.24(d, 1H), 6.60(d, 1H), 4.41(m, 1H), 3.76(br, 2H), 2.70(br, 2H), 2.47(br, 2H), 1.84(m, 4H) |
| 5-7 | 2-CH=CH—CH=CH-3 | 0 | CF$_3$ | H | 7.91-7.84(m, 2H), 7.68-7.47(m, 3H), 6.82(d, 1H), 4.96(m, 1H), 4.40-4.20(br, 2H) |

TABLE 6-continued ($R^1$ = H, t = 1)

| No. | Xn | m | $R^2$ | $R^3$ | $^1$H-NMR[CDCl$_3$/TMS, δ value(ppm)] |
|---|---|---|---|---|---|
| 5-8 | 2-CH(Me)CH$_2$CH$_3$ | 0 | CF$_3$ | H | 7.06-6.98(m, 2H), 6.67(d, 1H), 3.91(m, 1H), 3.85-3.70(br, 2H), 2.62(m, 1H), 1.78-1.50(m, 2H), 1.22(d, 3H), 0.89(t, 3H) |
| 5-9 | 2-CH(Me)CH$_2$CH$_2$CH$_3$ | 0 | CF$_3$ | H | 7.08-7.00(m, 2H), 6.67(d, 1H), 3.91(m, 1H), 3.82-3.70(br, 2H), 2.71(m, 1H), 1.70-1.50(m, 2H), 1.40-1.20(m, 5H), 0.90(t, 3H) |
| 5-10 | 2-CH(Me)CH$_2$CH$_2$CH$_3$ | 0 | CF$_3$ | OMe | 7.24(s, 1H), 7.16(d, 1H), 6.70(d, 1H), 4.00-3.82(br, 2H), 3.43(s, 3H), 2.73(m, 1H), 1.70-1.45(m, 2H), 1.40-1.20(m, 5H), 0.90(t, 3H) |
| 5-11 | 2-CH(Me)CH$_2$CHMe$_2$ | 0 | CF$_3$ | H | 7.10-7.00(m, 2H), 6.69(s, 1H), 3.91(m, 1H), 2.80(m, 1H), 1.65-1.50(m, 2H), 1.43-1.32(m, 1H), 1.21(d, 3H), 0.89(t, 6H) |
| 5-12 | 2-CH(Me)CH$_2$CHMe$_2$ | 0 | CF$_3$ | OH | 7.39(s, 1H), 7.30(d, 1H), 6.68(d, 1H), 3.90-3.60(br, 2H), 2.79(m, 1H), 1.61-1.50(m, 1H), 1.45-1.35(m, 1H), 1.21(d, 3H), 0.89(q, 6H) |
| 5-13 | 2-CH(Me)CH$_2$CHMe$_2$ | 0 | CF$_3$ | OMe | 7.26(s, 1H), 7.15(d, 1H), 6.70(d, 1H), 4.00-3.65(br, 2H), 3.43(s, 1H), 2.79(m, 1H), 1.56(m, 2H), 1.37(m, 1H), 1.20(d, 3H), 0.91(t, 6H) |
| 5-14 | 2-CH(Me)CH$_2$CHMe$_2$ | 0 | CF$_3$ | OEt | 7.26(s, 1H), 7.16(d, 1H), 6.69(d, 1H), 3.98-3.67(br, 2H), 3.59(q, 2H), 2.80(m, 1H), 1.56(m, 2H), 1.38(m, 1H), 1.30(t, 3H), 1.20(d, 3H), 0.89(t, 6H) |
| 5-15 | 2-CH(Me)CH$_2$CH$_2$CHMe$_2$ | 0 | CF$_3$ | H | 7.08-7.00(m, 2H), 6.68(d, 1H), 3.92(m, 1H), 3.99-3.70(br, 2H), 2.65(m, 1H), 1.78-1.42(m, 4H), 1.30-1.10(m, 5H), 0.86(d, 6H) |
| 5-16 | 2-CH(Me)CH$_2$CH$_2$CH$_2$CH$_3$ | 0 | CF$_3$ | H | 7.26(s, 1H), 7.20(d, 1H), 6.71(d, 1H), 3.95-3.78(br, 2H), 2.69(m, 1H), 1.72-1.42(m, 2H), 1.40-1.18(m, 7H), 0.88(t, 3H) |
| 5-17 | 2-CH(Me)CH$_2$CHMe$_2$ | 0 | H | H | 6.98(s, 1H), 6.92(d, 1H), 6.65(d, 1H), 3.85-3.60(br, 2H), 3.24(dd, 2H), 2.79(m, 1H), 1.65-1.48(m, 2H), 1.45-1.30(m, 1H), 1.19(d, 3H), 0.90(t, 6H) |
| 5-18 | 2-CH(Me)CH$_2$CHMe$_2$ | 2 | H | H | 6.97(s, 1H), 6.90(d, 1H), 6.65(d, 1H), 3.82-3.40(br, 2H), 3.23(t, 2H), 2.79(m, 1H), 1.70-1.50(m, 2H), 1.39(m, 1H), 1.20(d, 3H), 0.90(t, 6H) |
| 5-19 | 2-CH(Me)CH$_2$CHMe$_2$ | 4 | H | H | 6.97(s, 1H), 6.92(d, 1H), 6.65(d, 1H), 4.00-3.70(br, 2H), 3.24(t, 2H), 2.79(m, 1H), 1.68-1.48(m, 2H), 1.45-1.30(m, 1H), 1.22(d, 3H), 0.89(m, 6H) |
| 5-20 | 2-CH(Me)CH$_2$CHMe$_2$ | 6 | H | H | 6.97(s, 1H), 6.90(d, 1H), 6.65(d, 1H), 3.24(t, 2H), 2.79(m, 1H), 1.67-1.45(m, 2H), 1.42-1.30(m, 1H), 1.22(d, 3H), 0.90(t, 6H) |

Typical examples, formulation examples and test examples of the present invention are described below, but they should not be construed as limiting the scope of the invention.

EXAMPLE 1-1

Production of 2-(1,3-dimethylbutyl)-4-[2,2,2-trifluoro-1-(trifluoromethyl)ethyl]aniline (Compound No. 5-11)

Aluminum lithium hydride (2 g, 52.7 mmol) was suspended in tetrahydrofuran (60 ml), followed by adding dropwise thereto 2-(1,3-dimethylbutyl)-4-[1,2,2,2-tetrafluoro-1-(trifluoromethyl)ethyl]aniline (14 g, 40.5 mmol), and the resulting mixture was stirred at reflux temperature for 3 hours. Water was added to the reaction mixture in small portions under ice-cooling, followed by stirring for 10 minutes. Magnesium sulfate was added thereto and then stirred for 10 minutes. The reaction mixture was filtered through Celite and the filtrate was concentrated under reduced pressure to obtain 13 g of the desired compound.

Yield: 98%.

EXAMPLE 1-2

Production of N-{2-(1,3-dimethylbutyl)-4-[2,2,2-trifluoro-1-(trifluoromethyl)ethyl]phenyl}-5-chloro-1-methyl-3-trifluoromethylpyrazole-4-carboxamide (Compound No. 1-103)

5-Chloro-1-methyl-3-trifluoromethylpyrazole-4-carboxylic acid (230 mg, 1 mmol) was dissolved in thionyl chloride (2 ml), and the solution was stirred at reflux temperature for 2 hours. After concentration under reduced pressure, the resulting acid chloride was added to a solution of 2-(1,3-dimethylbutyl)-4-[2,2,2-trifluoro-1-(trifluoromethyl)ethyl]aniline (330 mg, 1 mmol) and triethylamine (150 mg, 1.5 mmol) in tetrahydrofuran (10 ml) under ice-cooling, and the resulting mixture was stirred at room temperature for 2 hours. The reaction mixture was diluted with ethyl acetate and then washed with water. The organic layer was dried over anhydrous magnesium sulfate and then concentrated under reduced pressure, and the resulting residue was separated and purified by silica gel column chromatography (hexane:ethyl acetate=3:1) to obtain 233 mg of the desired compound.
Physical property: melting point 102-104° C.
Yield: 43%.

EXAMPLE 2-1

Production of 2-(1,3-dimethylbutyl)-4-[1-methoxy-2,2,2-trifluoro-1-(trifluoromethyl)ethyl]-aniline (Compound No. 5-13)

Sodium (533 mg, 23 mmol) was dissolved in methanol (40 ml), followed by adding thereto 2-(1,3-dimethylbutyl)-4-[1,2,2,2-tetrafluoro-1-(trifluoromethyl)ethyl]aniline (2 g, 5.8 mmol), and the resulting mixture was stirred at reflux temperature for 3 hours. The reaction mixture was concentrated under reduced pressure, and the residue was diluted with ethyl acetate and washed with water. The organic layer was dried over magnesium sulfate and then concentrated under reduced pressure, and the resulting residue was separated and purified by silica gel column chromatography (hexane:ethyl acetate=6:1) to obtain 1.8 g of the desired compound.
Yield: 87%.

EXAMPLE 2-2

Production of N-{2-(1,3-dimethylbutyl)-4-[1-methoxy-2,2,2-trifluoro-1-(trifluoromethyl)ethyl]-phenyl}-1,3,5-trimethylpyrazole-4-carboxamide (Compound No. 1-108)

1,3,5-Trimethylpyrazole-4-carboxylic acid (154 mg, 1 mmol) was dissolved in thionyl chloride (5 ml), and the solution was heated under reflux for 2 hours. The reaction solution was concentrated under reduced pressure, and the resulting acid chloride was added to a solution of 2-(1,3-dimethylbutyl)-4-[1-methoxy-2,2,2-trifluoro-1-(trifluoromethyl)ethyl]-aniline (345 mg, 1 mmol) and triethylamine (150 mg, 1.5 mmol) in tetrahydrofuran (10 ml) under ice-cooling, after which the resulting mixture was heated under reflux for 2 hours. The reaction mixture was diluted with ethyl acetate and then washed with water. The organic layer was dried over anhydrous magnesium sulfate and then concentrated under reduced pressure, and the resulting residue was separated and purified by silica gel column chromatography. (hexane:ethyl acetate 1:2) to obtain 200 mg of the desired compound.
Physical property: melting point 94-96° C.
Yield: 41%.

EXAMPLE 3-1

Production of 2-(1-hydroxy-1,4-dimethylpentyl)aniline

Magnesium (960 mg, 40 mmol) and then a catalytic amount of iodine were added to diethyl ether (15 ml), followed by slowly adding thereto isoamyl bromide (6.04 g, 40 mmol) with refluxing, and the resulting mixture was stirred at reflux temperature for 30 minutes and then at room temperature for 30 minutes. To the resulting solution was added 2-aminoacetophenone (1.8 g, 13.3 mmol) under ice-cooling, followed by stirring at room temperature for 3 hours. Ammonium chloride was added thereto and the resulting mixture was diluted with ethyl acetate and washed with water. The organic layer was dried over magnesium sulfate and then concentrated under reduced pressure to obtain 2.7 g of 2-(1-hydroxy-1,4-dimethylpentyl)aniline.
Physical property: $^1$H-NMR [CDCl$_3$/TMS, δ values (ppm)]
7.10-7.00 (m, 2H), 6.72-6.60 (m, 2H), 4.00-3.70 (br, 2H), 2.03 (m, 2H), 1.61 (s, 3H), 1.50 (m, 2H), 1.20-1.00 (m, 1H), 0.90-0.83 (m, 6H).
Yield: 99%.

EXAMPLE 3-2

Production of 2-(1,4-dimethylpentyl)aniline

After 2.7 g (13.1 mols) of the 2-(1-hydroxy-1,4-dimethylpentyl)aniline obtained in Example 3-1 was diluted with toluene, p-toluenesulfonic acid monohydrate (225 mg) was added thereto, and the resulting mixture was dehydrated with refluxing over a period of 3 hours by the use of a Dean-Stark trap. The reaction mixture was diluted with ethyl acetate and then washed with an aqueous sodium hydrogencarbonate solution and saturated aqueous sodium chloride solution. The organic layer was dried over magnesium sulfate and then concentrated under reduced pressure. The resulting residue was dissolved in ethanol, followed by adding thereto 5% palladium-carbon (100 mg), and the resulting mixture was stirred under a hydrogen atmosphere at room temperature for 12 hours. The reaction mixture was filtered through Celite and the residue was concentrated under reduced pressure to obtain 2.2 g of 2-(1,4-dimethylpentyl)aniline.
Physical property: $^1$H-NMR [CDCl$_3$/TMS, δ values (ppm)]
7.10 (dd, 2H), 7.02 (dt, 1H), 6.79 (dt, 1H), 6.69 (dd, 1H), 3.67 (bs, 2H), 2.68 (m, 1H), 1.80-1.42 (m, 4H), 1.30-1.10 (m, 5H), 0.87 (d, 6H).
Yield: 87%.

EXAMPLE 3-3

Production of 2-(1,4-dimethylpentyl)-4-[1,2,2,2-tetrafluoro-1-(trifluoromethyl)ethyl]aniline The 2-(1,4-dimethylpentyl)aniline (1.8 g, 9.4 mmol) obtained in Example 3-2 was dissolved in a solution (50 ml) consisting of t-butyl methyl ether and water in the ratio of 1:1. To the resulting solution were added 1,2,2,2-tetrafluoro-1-(trifluoromethyl)ethyl iodide (2.78 g, 9.4 mmol), tetra-n-butylammonium hydrogensulfate (318 mg, 0.94 mmol), sodium hydrogencarbonate (795 mg, 9.4 mmol) and then sodium dithionite (1.63 g, 9.4 mmol), and the resulting mixture was stirred at room temperature for 12 hours. The reaction mixture was diluted with hexane and washed twice with 3N hydrochloric acid and then with an aqueous sodium hydrogencarbonate solution and saturated aqueous sodium chloride solution. The organic layer was dried over magnesium sulfate and then concentrated under reduced pressure to obtain 3.28 g of the desired compound.
Physical property: $^1$H-NMR [CDCl$_3$/TMS, δ values (ppm)]
7.26 (s, 1H), 7.21 (d, 1H), 6.72 (d, 1H), 4.05-3.80 (br, 2H), 2.67 (m, 1H), 1.78-1.40 (m, 4H), 1.30-1.00 (m, 5H), 0.85 (d, 6H).
Yield: 97%.

EXAMPLE 3-4

Production of 2-(1,4-dimethylpentyl)-4-[2,2,2-trifluoro-1-(trifluoromethyl)ethyl]aniline (Compound No. 5-15)

The desired compound was obtained by carrying out reaction for 4 hours in the same manner as in Example 1-1 except for using 2-(1,4-dimethylpentyl)-4-[1,2,2,2-tetrafluoro-1-

(trifluoromethyl)ethyl]aniline in place of 2-(1,3-dimethylbutyl)-4-[1,2,2,2-tetra-fluoro-1-(trifluoromethyl)ethyl]aniline.
Yield: 82%.

EXAMPLE 3-5

Production of N-{2-(1,4-dimethylpentyl)-4-[2,2,2-trifluoro-1-(trifluoromethyl)ethyl]phenyl}-5-chloro-1,3-dimethylpyrazole-4-carboxamide (Compound No. 1-146)

5-Chloro-1,3-dimethylpyrazole-4-carboxylic acid (349 mg, 2 mmol) was dissolved in thionyl chloride (10 ml), and the solution was stirred at reflux temperature for 2 hours. After concentration under reduced pressure, the resulting acid chloride was added to a solution of 2-(1,4-dimethylpentyl)-4-[2,2,2-trifluoro-1-(trifluoromethyl)ethyl]aniline (682 mg, 2 mmol) and triethylamine (300 mg, 3 mmol) in tetrahydrofuran (20 ml) under ice-cooling, and the resulting mixture was stirred at reflux temperature for 2 hours. The reaction mixture was diluted with ethyl acetate and then washed with water. The organic layer was dried over anhydrous magnesium sulfate and then concentrated under reduced pressure, and the resulting residue was separated and purified by silica gel column chromatography (hexane:ethyl acetate=2:3) to obtain 200 mg of the desired compound.
Physical property: refractive index 1.4905 (20.4° C.).
Yield: 41%.

EXAMPLE 4-1

Production of 4-iodo-2-(1,3-dimethylbutyl)aniline

In methanol was dissolved 2.53 g (10 mmol) of iodine, and 2-(1,3-dimethylbutyl)aniline (1.77 g, 10 mmol) was added thereto under ice-cooling, after which an aqueous solution of sodium hydrogencarbonate (1.26 g, 15 mmol) was added thereto and the resulting mixture was stirred at 0° C. for 4 hours. Sodium thiosulfate was added to the reaction mixture, and the resulting mixture was concentrated under reduced pressure, diluted with ethyl acetate and then washed with water. The organic layer was dried over magnesium sulfate and the residue was separated and purified by silica gel column chromatography (hexane:ethyl acetate=10:1) to obtain 2.71 g of the desired compound.
Yield: 89%.

EXAMPLE 4-2

Production of 2-(1,3-dimethylbutyl)-4-pentafluoroethylaniline

4-Iodo-2-(1,3-dimethylbutyl)aniline (1.35 g, 4.45 mmol), copper powder (0.85 g, 13.4 mmol) and pentafluoroethyl iodide (1.42 g, 5.77 mmol) were added to dimethyl sulfoxide (10 ml), and the resulting mixture was stirred at 130° C. for 4 hours. The mixture was filtered through Celite and the filtrate was diluted with ethyl acetate and washed 4 times with water. The organic layer was dried over magnesium sulfate and then concentrated under reduced pressure to obtain 1.24 g of the desired compound.
Physical property: $^1$H-NMR [CDCl$_3$/TMS, δ values (ppm)]
7.26 (s, 1H), 7.20 (d, 1H), 6.70 (d, 1H), 4.00-3.85 (br, 2H), 3.00 (m, 1H), 1.68-1.50 (m, 2H), 1.48-1.30 (m, 1H), 1.22 (t, 3H), 0.94 (m, 6H)
Yield: 95%.

EXAMPLE 4-3

Production of 2-(1,3-dimethylbutyl)-4-(2,2,2-trifluoroethyl)aniline (Compound No. 5-17)

Aluminum lithium hydride (1.62 g, 4.26 mmol) was dissolved in tetrahydrofuran (20 ml), followed by adding dropwise thereto 2-(1,3-dimethylbutyl)-4-pentafluoroethylaniline (974 mg, 3.3 mmol), and the resulting mixture was stirred at reflux temperature for 3 hours. Water was added to the reaction mixture in small portions under ice-cooling, followed by stirring for 10 minutes. Magnesium sulfate was added thereto and then stirred for 10 minutes. The reaction mixture was filtered through Celite and the filtrate was concentrated under reduced pressure, after which the residue was separated and purified by silica gel column chromatography (hexane:ethyl acetate=9:1) to obtain 260 mg of the desired compound.
Yield: 30%.

EXAMPLE 5-1

Production of 2-(1,3-dimethylbutyl)-4-nonafluorobutylaniline

The desired compound was obtained by carrying out reaction for 4 hours in the same manner as in Example 4-2 except for using nonafluorobutyl iodide in place of pentafluoroethyl iodide.
Physical property: $^1$H-NMR [CDCl$_3$/TMS, δ values (ppm)]
7.25 (s, 1H), 7.20 (d, 1H), 6.71 (d, 1H), 4.02-3.85 (m, 2H), 2.79 (m, 1H), 1.68-1.50 (m, 2H), 1.50-1.35 (m, 1H), 1.22 (d, 3H), 0.90 (t, 6H)
Yield: 90%.

EXAMPLE 5-2

Production of 2-(1,3-dimethylbutyl)-4-(2,2,3,3,4,4,4-heptafluorohexyl)aniline (Compound No. 5-18)

The desired compound was obtained by stirring for 3 hours in the same manner as in Example 4-3 except for using 2-(1,3-dimethylbutyl)-4-nonafluorobutylaniline in place of 2-(1,3-dimethylbutyl)-4-pentafluoroethylaniline.
Yield: 92%.

EXAMPLE 6-1

Production of 2-(1,3-dimethylbutyl)-4-tridecafluorohexylaniline

The desired compound was obtained by carrying out reaction for 4 hours in the same manner as in Example 4-2 except for using tridecafluorohexyl iodide in place of pentafluoroethyl iodide.
Physical property: $^1$H-NMR [CDCl$_3$/TMS, δ values (ppm)]
7.25 (s, 1H), 7.20 (d, 1H), 6.71 (d, 1H), 4.05-3.87 (m, 2H), 2.79 (m, 1H), 1.68-1.50 (m, 2H), 1.48-1.30 (m, 1H), 1.22 (d, 3H), 0.90 (t, 6H)
Yield: 87%.

EXAMPLE 6-2

Production of 2-(1,3-dimethylbutyl)-4-(2,2,3,3,4,4,5,5,6,6,6-undecafluorohexyl)aniline (Compound No. 5-19)

The desired compound was obtained by stirring for 3 hours in the same manner as in Example 4-3 except for using 2-(1,3-dimethylbutyl)-4-tridecafluorohexylaniline in place of 2-(1,3-dimethylbutyl)-4-pentafluoroethylaniline.
Yield: 85%.

EXAMPLE 7-1

Production of 2-(1,3-dimethylbutyl)-4-heptadecafluorooctylaniline

The desired compound was obtained by carrying out reaction for 4 hours in the same manner as in Example 4-2 except for using heptadecafluorooctyl iodide in place of pentafluoroethyl iodide.

Physical property: $^1$H-NMR [CDCl$_3$/TMS, δ values (ppm)]
7.24 (s, 1H), 7.19 (d, 1H), 6.70 (d, 1H), 4.05-3.85 (br, 2H), 2.78 (m, 1H), 1.67-1.50 (m, 3H), 1.50-1.32 (m, 1H), 1.21 (d, 3H), 0.89 (t, 6H).

Yield: 40%.

EXAMPLE 7-2

Production of 2-(1,3-dimethylbutyl)-4-(2,2,3,3,4,4,5,5,6,6,6-pentadecafluorooctyl)aniline (Compound No. 5-20)

The desired compound was obtained by stirring for 3 hours in the same manner as in Example 4-3 except for using 2-(1,3-dimethylbutyl)-4-heptadecafluorooctylaniline in place of 2-(1,3-dimethylbutyl)-4-pentafluoroethylaniline.

Yield: 58%.

The agrohorticultural agent, in particular, agrohorticultural insecticide or acaricides, containing the substituted anilide derivative represented by the formula (I) or salt thereof of the present invention as an active ingredient, are suitable for controlling various insect pests such as agrohorticultural insect pests, stored grain insect pests, sanitary insect pests, nematodes, etc., which are injurious to paddy rice, fruit trees, vegetables, other crops, flowers, ornamental plants, etc. They have a marked insecticidal effect, for example, on LEPIDOPTERA including summer fruit tortrix (*Adoxophes orana fasciata*), smaller tea tortrix (*Adoxophyes* sp.), Manchurian fruit moth (*Grapholita inopinata*), oriental fruit moth (*Grapholita molesta*), soybean pod borer (*Leguminovora glycinivorella*), mulberry leafroller (*Olethreutes mori*), tea leafroller (*Caloptilia thevivora*), *Caloptilia* sp. (*Caloptilia zachrysa*), apple leafminer (*Phyllonorycter ringoniella*), pear barkminer (*Spulerrina astaurota*), common white (*Piers rapae crucivora*), tobacco budworm (*Heliothis* sp.), codling moth (*Laspey resia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tobacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticepts*), brown rice planthopper (*Nilaparvata lugens*), whitebacked rice planthopper (*Sogatella furcifera*), citrus psylla (*Diaphorina citri*), grape whitefly (*Aleurolibus taonabae*), sweet-potato whitefly (*Bemisia tabaci*), greenhouse whitefly (*Trialeurodes vaporariorum*), turnup aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), san Jose scale (*Comstockaspis perniciosa*), arrowhead scale (*Unapsis yanonensis*), etc.; TYLENCHIDA including root-lesion nematoda (*Pratylenchus* sp.), soybean beetle (*Anomala rufocuprea*), Japanese beetle (*Popillia japonica*), tobacco beetle (*Lasioderma serricorne*), powderpost beetle (*Lyctus brunneus*), twenty-eight-spotted ladybird (*Epilachna vigintiotopunctata*), azuki bean weevil (*Callosobruchus chinensis*), vegetable weevil (*Listroderes costirostris*), maize weevil (*Sitophilus zeamais*), boll weevil (*Anthonomus grandis grandis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica* sp.), etc.; DIPTERA including (*Dacus(Zeugodacus) cucurbitae*), oriental fruit fly (*Dacus(Bactrocera) dorsalis*), rice leafminer (*Agnomyza oryzae*), onion maggot (*Delia antiqua*), seedcorn maggot (*Delia platura*), soybean pod gall midge (*Asphondylia* sp.), muscid fly (*Musca domestica*), house mosquito (*Culex pipiens pipiens*), etc.; TYLENCHIDA including root-lesion nematode (Pratylenchus sp.), coffee root-lesion nematode (*Pratylenchus coffeae*), potato cyst nematode (*Globodera rostochiensis*), root-knot nematode (Meloidogyne sp.), citrus nematode (*Tylenchulus semipenetrans*), Aphelenchus sp. (*Aphelenchus avenae*), chrysanthemum foliar (*Aphelenchoides ritzemabosi*), etc.; and ACARINA including citrus red mite (*Panonychus citri*), fruit tree red spider mite (*Panonychus ulmi*), carmine spider mite (*Tetranychus cinnabarinus*), Kanzawa spider mite (*Tetranychus Kanzawai Kishida*), two-spotted spider mite (*Tetranychus urticae Koch*), pink tea rust mite (*Acaphylla theae*), pink citrus rust mite (*Aculops pelekassi*), purple tea mice (*Calacarus carinatus*), pear rust mite (*Epitrimerus pyri*), etc.

The agrohorticultural agent containing a substituted anilide derivatives represented by general formula (I) is also useful as an agrohorticultural fungicide, and they exhibit a very high fungicidal effect against various diseases. Specific examples of the diseases against which the compounds of the present invention exhibit a marked effect include rice blast (*Pyricularia oryzae*), rice sheath blight (*Rhizoctonia solani*), rice helminthosporium leaf spot (*Cochiobolus miyabeanus*), powdery mildew of various host plants such as powdery mildew of barley and wheat (*Erysiphe graminis*), oats crown rust (*Puccinia coronata*), stem rust of other plants, late blight of tomato (*Phytophthora infestans*), late blight of other plants, late blight or Phytophthora rots of various plants such as cucumber downy mildew (*Pseudoperonospora cubensis*), grape downy mildew (*Plasmopara viticola*), etc., apple scab (*Venturia inaegualis*), apple alternaria leaf spot (*Alternaria mali*), pear black spot (*Alternaria kikuchiana*), citrus melanose (*Diaporthe citri*), bacterial diseases due to Genus Pseudomonas such as cucumber bacterial blight (*Pseudomonas syringae* pv. *lachrymans*) and tomato bacterial wilt (*Pseudomonas solanacearum*), bacterial diseases due to Genus *Xanthomonas* such as cabbage black rot (*Xanthomonas campestris*), rice bacterial leaf blight (*Xanthomonas oryzae*) and citrus canker (*Xanthomonas citri*), and bacterial diseases due to Genus *Erwinia* such as cabbage bacterial soft rot (*Erwinia carotovora*), and viral diseases such as tobacco mosaic (tobacco mosaic virus), etc.

The agrohorticultural agent, in particular, agrohorticultural insecticide, which contains as an active ingredient the substituted anilide derivative of the general formula (I) or salt thereof of the present invention has a marked insecticidal effect on the above-exemplified insect pests injurious to paddy field crops, upland crops, fruit trees, vegetables, other crops, flowers and ornamental plants, and the like. Therefore, the desired effect of the agrohorticultural agent, in particular, agrohorticultural insecticide of the present invention can be obtained by applying the present agrohorticultural agent to the paddy field water, stalks and leaves of fruit trees, vegetables, other crops, flowers and ornamental plants, soil, etc., at a season at which the insect pests are expected to appear, before their appearance or at the time when their appearance is confirmed.

The agrohorticultural agent of the present invention is generally prepared into conveniently usable forms according to an ordinary manner for preparation of agrochemicals.

That is, the substituted anilide derivative of the general formula (I) or a salt thereof and, optionally, an adjuvant are blended with a suitable inert carrier in a proper proportion and prepared into a suitable preparation form such as a suspension, emulsifiable concentrate, soluble concentrate, wettable powder, granules, dust, tablets, pack or the like through dissolution, dispersion, suspension, mixing, impregnation, adsorption or sticking.

The inert carrier usable in the present invention may be either solid or liquid. As a material usable as the solid carrier, there can be exemplified soybean flour, cereal flour, wood flour, bark flour, saw dust, powdered tobacco stalks, powdered walnut shells, bran, powdered cellulose, extraction residue of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica and white carbon [synthetic, high-dispersion silicic acid, also called finely divided hydrated silica or hydrated silicic acid, some of commercially available products contain calcium silicate as the major component]), activated carbon, powdered sulfur, pumice, calcined diatomaceous earth, ground brick, fly ash, sand, calcium carbonate, calcium phosphate and other inorganic or mineral powders, chemical fertilizers (e.g. ammonium sulfate, ammonium phosphate, ammonium nitrate, urea and ammonium chloride), and compost. These carriers may be used alone or as a mixture thereof.

A material usable as the liquid carrier is selected from materials that have solubility in themselves or which are without such solubility but are capable of dispersing an active ingredient with the aid of an adjuvant. The following are typical examples of the liquid carrier and can be used alone or as a mixture thereof: water, alcohols (e.g. methanol, ethanol, isopropanol, butanol and ethylene glycol), ketones (e.g. acetone, methyl ethyl ketone, methyl isobutyl ketone, diisobutyl ketone and cyclohexanone), ethers (e.g. ethyl ether, dioxane, Cellosolve, dipropyl ether and tetrahydrofuran), aliphatic hydrocarbon (e.g. kerosene and mineral oils), aromatic hydrocarbons (e.g. benzene, toluene, xylene, solvent naphtha and alkylnaphthalenes), halogenated hydrocarbons (e.g. dichloroethane, chloroform, carbon tetrachloride and chlorobenzene), esters (e.g. ethyl acetate, diisopropyl phthalate, dibutyl phthalate and dioctyl phthalate), amides (e.g. dimethylformamide, diethylformamide and dimethylacetamide), nitriles (e.g. acetonitrile), and dimethyl sulfoxide.

The following are typical examples of the adjuvant, which are used depending upon purposes and used alone or in combination is some cases, or need not be used at all.

To emulsify, disperse, dissolve and/or wet a compound as active ingredient, a surfactant is used. As the surfactant, there can be exemplified polyoxyethylene alkyl ethers, polyoxyethylene alkylaryl ethers, polyoxyethylene higher fatty acid esters, polyoxyethylene resonates, polyoxyethylene sorbitan monolaurate, polyoxyethylene sorbitan monooleate, alkylarylsulfonates, naphthalene sulfonic acid condensation products, ligninsulfonates and higher alcohol sulfate esters.

Further, to stabilize the dispersion of a compound as active ingredient, tackify it and/or bind it, the adjuvants exemplified below may also be used, namely, there may also be used adjuvants such as casein, gelatin, starch, methyl cellulose, carboxymethyl cellulose, gum arabic, poly(vinyl alcohol)s, turpentine, bran oil, bentonite and ligninsulfonates.

To improve the flowability of a solid product, the following adjuvants may also be used, namely, there may be used adjuvants such as waxes, stearates, alkyl phosphates, etc.

Adjuvants such as naphthalenesulfonic acid condensation products and polycondensates of phosphates may be used as a peptizer for dispersible products.

Adjuvants such as silicone oils may also be used as a defoaming agent.

Adjuvants such as 1,2-benzisothiazoline-3-one, 4-chloro-3,5-xylenol, butyl p-hydroxybenzoate may also be added as a preservative.

Further, if necessary, functional spreading agents, active enhancers such as metabolic decomposition inhibitor like piperonyl butoxide, anti-freezing agents such as propylene glycol, antioxidants such as BHT, ultraviolet absorbers, and the like may also be added.

The content of the compound as active ingredient may be varied as required, and the compound as active ingredient may be used in a proportion properly chosen in the range of 0.01 to 90 parts by weight per 100 parts of the agrohorticultural agent. For example, in dusts or granules, the suitable content of the compound as active ingredient is from 0.01 to 50% by weight. In emulsifiable concentrates or flowable wettable powders, it is also from 0.01 to 50% by weight.

The agrohorticultural agent of the present invention is used to control a variety of insect pests in the following manner: it is applied to a crop on which the insect pests are expected to appear, or a site where appearance or growth of the insect pests is undesirable, as it is or after being properly diluted with or suspended in water or the like, in an amount effective for control of the insect pests.

The applying dosage of the agrohorticultural insecticide of the present invention is varied depending upon various factors such as a purpose, insect pests to be controlled, a growth state of a plant, tendency of insect pests appearance, weather, environmental conditions, a preparation form, an application method, an application site and application time. It may be properly chosen in the range of 0.001 g to 10 kg, preferably 0.01 g to 1 kg, (in terms of the compound as active ingredient) per 10 ares depending upon purposes.

The agrohorticultural agent of the present invention may be used in admixture with other agrohorticultural insecticides, acaricides, nematocides, fungicides, biotic pesticides or the like in order to expand both spectrum of controllable insect pest species and the period of time when effective application are possible or to reduce the dosage. Furthermore, the agrohorticultural agent of the present invention may be used in admixture with herbicides, plant growth regulators, fertilizers or the like, depending upon application situations.

As the other agrohorticultural insecticides, acaricides and nematocides, which are used for the above purpose, there can be exemplified agrohorticultural insecticides, acaricides and nematocides, such as Ethion, Trichlorfon, Metamidophos, Acephate, Dichlorvos, Mevinphos, Monocrotophos, Malathion, Dimethoate, Formothion, Mecarbam, Vamidothion, Thiometon, Disulfoton, Oxydeprofos, Naled, Methylparathion, Fenitrothion, Cyanophos, Propaphos, Fenthion, Prothiofos, Profenofos, Isofenphos, Temephos, Phenthoate, Dimethylvinphos, Chlorfenvinphos, Tetrachlorvinphos, Phoxim, Isoxathion, Pyraclofos, Methidathion, Chlorpyrifos, Chlorpyrifos-methyl, Pyridaphenthion, Diazinon, Pirimiphosmethyl, Phosalone, Phosmet, Dioxabenzophos, Quinalphos, Terbuphos, Ethoprophos, Cadusafos, Mesulfenfos, DPS (NK-0795), Phosphocarb, Fenamiphos, Isoamidophos, Fosthiazate, Isazophos, Ethoprophos, Fenthion, Fostietane, Dichlofenthion, Thionazin, Sulprofos, Fensulfothion, Diamidafos, Pyrethrin, Allethrin, Prallethrin, Resmethrin, Permethrin, Tefluthrin, Bifenthrin, Fenpropathrin, Cypermethrin, α-Cypermethrin, Cyhalothrin, λ-Cyhalothrin, Deltamethrin, Acrinathrin, Fenvalerate, Esfenvalerate, Flucythrinate, Fluvalinate, Cycloprothrin, Ethofenprox, Halfenprox, Silafluofen, Fluvalinate, Methomyl, Oxamyl, Thiodicarb, Aldicarb, Alanycarb, Cartap, Metolcarb, Xylylcarb, Propoxur, Phenoxycarb, Fenobucarb, Ethiophencarb, Fenothiocarb, Bifenazate, BPMC, Carbaryl, Pirimicarb, Carbofuran, Carbosulfan, Furathiocarb, Benfuracarb, Aldoxycarb, Diafenthiuron, Diflubenzuron, Teflubenzuron, Hexaflumuron, Novaluron, Lufenuron, Flufenoxuron, Chlorfluazuron, Fenbutatin oxide, tricyclohexyltin hydroxide, sodium oleate, potassium oleate, Methoprene, Hydroprene, Binapacryl, Amitraz, Dicofol, Kersen, Chrorobenzilate, Bromopropylate, Tetradifon, Bensultap, Benzoximate, Tebufenozide, Methoxyfenozide, Chromafenozide, Propargite, Acequinosyl, Endosulfan, Diofenolan, Chlorfenapyl, Fenpyroximate, Tolfenpyrad, Fipronil, Tebufenpyrad, Triazamate, Etoxazole, Hexythiazox, nicotine sulfate, Nitenpyram, Acetamiprid, Thiacloprid, Imidacloprid, Thiamethoxam, Clothianidin, Nidinotefuran, Fluazinam, Pyriproxyfen, Hydramethylnon, Pyrimidifen, Pyridaben, Cyromazin, TPIC (tripropyl isocyanurate), Pymetrozin, Clofentezin, Buprofedin, Thiocyclam, Fenazaquin, Chinomethionate, Indoxacarb, Polynactin complexes, Milbemectin, Abamectin, Emamectin-benzoate, Spinosad, BT (*Bacillus thuringiensis*), Azadirachtin, Rotenone, hydroxypropyl starch, Levamisole hydrochloride, Metam-sodium, Morantel tartrate, Dazomet, Trichlamide, Pasteuria penetrans, Monacrosporium-phymatophagum, etc. As the agrohorticultural fungicides used for the same purpose as above, there can be exemplified agrohorticultural fungicides such as sulfur, lime sulfur, copper sulfate basic, Iprobenfos, Edifenfos, Tolclofosmethyl, Thiram, Polycarbamate, Zineb, Maneb, Mancozeb, Propineb, Thiophanate, Thiophanate methyl, Benomyl, Iminoctadin acetate, Iminocutadin albecylate, Mepronil, Flutolanil, Pencycuron, Furametpyl, Thifluzamide, Metalaxyl, Oxadixyl, Carpropamid, Dichlofluanid, Flusulfamide, Chlorothalonil, Kresoxim-methyl, Fenoxanil (NNF-9425), Himexazol, Etridiazol, Fluoroimide, Procymidone, Vinclozolin, Iprodione, Triadimefon, Triflumizole, Bitertanol, Ipconazole, Fluconazole, Propiconazole, Diphenoconazole, Myclobutanil, Tetraconazole, Hexaconazole, Tebuconazole, Imibenconazole, Prochloraz, Pefurazoate, Cyproconazole, Isoprothiolane, Fenarimol, Pyrimetanil, Mepanipyrim, Pyrifenox, Fluazinam, Triforine, Diclomezine, Azoxystrobin, Thiadiazin, Captan, Probenazole, Acibenzolar-S-methyl (CGA-245704), Fthalide, Tricyclazole, Pyroquilon, Chinomethionat, Oxolinic acid, Dithianon, Kasugamycin, Validamycin, Polyoxin, Blasticidin, Streptomycin, etc. Similarly, as the herbicides, there can be exemplified herbicides such as Glyphosate, Sulfosate, Glyfosinate, Bialaphos, Butamifos, Esprocarb, Prosulcarb, Benthiocarb, Pyributycarb, Asulam, Linulon, Dymron, Bensulfuron methyl, Cyclosulfamuron, Cinosulfuron, Pyrazosulfuron ethyl, Azimsulfuron, Imazosulfuron, Tenylchlor, Alachlor, Pretilachlor, Clomeprop, Etobenzanid, Mefenacet, Pendimethalin, Bifenox, Acifluorfen, Lactfen, Cyhalofop-butyl, Ioxynil, Bromobutide, Alloxydim, Setoxydim, Napropamide, Indanofan, Pyrazolate, Benzofenap, Pyraflufen-ethyl, Imazapyl, Sulfentrazone, Cafenstrole, Bentoxazon, Oxadiazon, Paraquat, Diquat, Pyriminobac, Simazine, Atrazine, Dimethametryn, Triazyflam, Benflesate, Flutiacetmethyl, Quizalofop-ethyl, Bentazon, calcium peroxide, etc.

As to the biotic pesticides, the same effect as above can be expected by using the agrohorticultural agent of the present invention in admixture with, for example, viral formulations obtained from nuclear polyhedrosis virus (NPV), granulosis virus (GV), cytoplasmic polyhedrosis virus (CPV), entomopox virus (EPV), etc.; microbial pesticides utilized as insecticides or nematicides, such as *Monacrosporium phymatophagum, Steinernema carpocapsae, Steinernema kushidai, Pasteuria penetrans*, etc.; microbial pesticides utilized as fungicides, such as *Trichoderma lignorum, Agrobacterium radiobactor*, nonpathogenic *Erwinia carotovora, Bacillus subtilis*, etc.; and biotic pesticides utilized as herbicides, such as *Xanthomonas campestris*, etc.

In addition, the agrohorticultural agent of the present invention can be used in combination with biotic pesticides including natural enemies such as Parasitic wasp (*Encarsia formosa*), Parasitic wasp (*Aphidius colemani*), Gall-mildge (*Aphidoletes aphidimyza*), Parasitic wasp (*Diglyphus isaea*), Parasitic mite (*Dacnusa sibirica*), Predatory mite (*Phytoseiulus persimilis*), Predatory mite (*Amblyseius cucumeris*), Predatory bug (*Orius sauteri*), etc.; microbial pesticides such as Beauveria brongniartii, etc.; and pheromones such as (Z)-10-tetradecenyl=acetate, (E,Z)-4,10-tetradecadienyl=acetate, (Z)-8-dodecenyl=acetate, (Z)-11-tetradecenyl=acetate, (Z)-13-icosen-10-one, (Z)-8-dodecenyl=acetate, (Z)-11-tetradecenyl=acetate, (Z)-13-icosen-10-one, 14-methyl-1-octadecene, etc.

Typical examples of the present invention are described below but they should not be construed as limiting the scope of the invention.

As used in the examples, the terms "part" and "parts" are by weight.

FORMULATION EXAMPLE 1

| | |
|---|---|
| Each compound listed in Tables 1 to 4 | 10 parts |
| Xylene | 70 parts |
| N-methylprrolidone | 10 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

FORMULATION EXAMPLE 2

| | |
|---|---|
| Each compound listed in Tables 1 to 4 | 3 parts |
| Clay powder | 82 parts |
| Diatomaceous earth powder | 15 parts |

A dust was prepared by mixing uniformly and grinding the above ingredients.

FORMULATION EXAMPLE 3

| | |
|---|---|
| Each compound listed in Tables 1 to 4 | 5 parts |
| Mixed powder of bentonite and clay | 90 parts |
| Calcium ligninsulfonate | 5 parts |

Granules were prepared by mixing the above ingredients uniformly, and kneading the resulting mixture together with a suitable amount of water, followed by granulation and drying.

FORMULATION EXAMPLE 4

| Each compound listed in Tables 1 to 4 | 20 parts |
|---|---|
| Mixture of kaolin and synthetic kaoline and high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

TEST EXAMPLE 1

Insecticidal Effect on Diamond Back Moth (*Plutella xylostella*)

Adult diamond back moths were released and allowed to oviposit on a Chinese cabbage seedling. Two days after the release, the seedling having the eggs deposited thereon was immersed for about 30 seconds in a liquid chemical prepared by diluting a preparation containing each compound listed in Tables 1 to 4 as an active ingredient to adjust the concentration to 500 ppm. After air-dryness, it was allowed to stand in a room thermostatted at 25° C. Six days after the immersion, the hatched insects were counted. The mortality was calculated according to the following equation and the insecticidal effect was judged according to the criterion shown below. The test was carried out with triplicate groups of 10 insects.

$$\text{Corrected mortality (\%)} = \frac{\text{Number of hatched insects in untreated group} - \text{Number of hatched insects in treated group}}{\text{Number of hatched insects in untreated group}} \times 100$$

Criterion:
A—Mortality 100%
B—Mortality 99-90%
C—Mortality 89-80%
D—Mortality 79-50%

As a result, the following compounds were rated B or higher: compound Nos. 1-2,1-4, 1-10, 1-14, 1-17, 1-20, 1-21, 1-26, 1-28, 1-33, 1-35, 1-41, 1-48, 1-52, 1-56, 1-57, 1-58, 1-65, 1-70, 1-73, 1-82, 1-103, 1-107, 1-108, 1-132, 1-133, 1-143, 1-145, 1-146, 1-163, 1-164, 3-2,3-3, 3-4,3-10, 3-12, 4-1,4-4, and 4-5.

TEST EXAMPLE 2

Insecticidal Effect on Smaller Tea Tortrix (*Adxophyes* sp.)

Tea leaves were immersed for about 30 seconds in a liquid chemical prepared by diluting a preparation containing each compound listed in Tables 1 to 4 as an active ingredient to adjust the concentration to 500 ppm. After air-dryness, the tea leaves were placed in a plastic Petri dish with a diameter of 9 cm and inoculated with larvae of smaller tea tortrix, after which the dish was allowed to stand in a room thermostatted at 25° C. and having a humidity of 70%. Eight days after the inoculation, the dead and alive were counted. The mortality was calculated according to the following equation and the insecticidal effect was judged according to the criterion shown in Test Example 1. The test was carried out with triplicate groups of 10 insects.

$$\text{Corrected mortality (\%)} = \frac{\text{Number of alive larvae in untreated group} - \text{Number of alive larvae in treated group}}{\text{Number of alive larvae in untreated group}} \times 100$$

As a result, the following compounds were rated B or higher: compound Nos. 1-52, 1-60, 1-103, 3-12, 3-28, 3-30 and 3-31.

TEST EXAMPLE 3

Acaricidal Effect on Two-Spotted Spider Mite (*Tetranychus Urticae*)

A leaf disc with a diameter of 2 cm was made of a kidney bean leaf, placed on wet filter paper, inoculated with female adult two-spotted spider mites, and then uniformly sprayed, on a turntable, with 50 ml of a liquid chemical prepared by diluting a preparation containing each compound listed in Tables 1 to 4 as an active ingredient to adjust the concentration to 500 ppm. After the spraying, the leaf disc was allowed to stand in a room thermostated at 25° C. Two days after the treatment with the preparation, the dead insects were counted and the acaricidal effect was judged according to the criterion shown in Test Example 1. The test was carried out with two replications of 10 insects.

As a result of the above test, it was found that the following compounds had an activity rated B or higher: 1-22, 1-23, 1-25, 1-26, 1-34, 1-39, 1-40, 1-51, 1-52, 1-54, 1-60 to 1-62, 1-65, 1-70 to 1-73, 1-78, 1-81, 1-82, 1-103, 1-104, 1-106 to 1-109, 1-119, 1-132, 1-143, 1-146, 3-13, 3-21, 3-30 to 3-32, and 4-3.

TEST EXAMPLE 4

Insecticidal Effect on Green Peach Aphid (*Myzus Persicae*)

A Chinese cabbage plant was planted in each of plastic pots with a diameter of 8 cm and a height of 8 cm, and green peach aphids were propagated on the plant. Then, the stems and leaves were sufficiently sprayed with a liquid chemical prepared by diluting a preparation containing each compound listed in Tables 1 to 4 as an active ingredient to adjust the concentration to 500 ppm. After air-drying, the pots were allowed to stand in a greenhouse. Six days after the spraying, green peach aphids parasitic on each Chinese cabbage plant were counted and the control efficacy was calculated, whereby the acaricidal effect was judged according to the criterion shown below.

Control efficacy (%)=100−[($T$×$Ca$)/($Ta$×$C$)]×100

Ta: number of parasites before spraying in treated group,
T: number of parasites after spraying in treated group,
Ca: number of parasites before spraying in untreated group,
T: number of parasites after spraying in untreated group.

Criterion for Judgment:
A: control efficacy 100%
B: control efficacy 99 to 90%
C: control efficacy 89 to 80%
D: control efficacy 79 to 50%

As a result of the above test, it was found that the following compounds had an activity rated B or higher: 1-4,1-8, 1-25, 1-35, 1-41, 1-52, 1-65, 1-81, 1-87, 1-106 to 1-108, 1-146, 3-27, 3-13, 3-34 and 4-1.

TEST EXAMPLE 5

Controlling Effect on Barley Powdery Mildew

Potted barley plants at the 1 leaf stage were inoculated with spores of powdery mildew fungus (*Erysiphe graminis hordei*) by sprinkling. After one day, they were sprayed with a liquid chemical prepared by diluting a preparation containing each compound listed in Table 1, Table 3 or Table 4 as an active ingredient to adjust the concentration to 200 ppm. Then, they were allowed to stand in a room thermostated at 25° C. One week after the inoculation, the lesion area of each leaf was measured and then compared with that on the untreated plot, whereby the controlling effect was judged according to the following criterion.

Criterion for Judgment:
A: control efficacy 100 to 95%
B: control efficacy 94 to 80%
C: control efficacy 79 to 60%
D: control efficacy 59 to 0%

As a result of the above test, it was found that the following compounds had an activity rated B or higher: 1-5,1-12, 1-23, 1-30, 1-45, 1-47, 1-52, 1-54, 1-83, 1-133, 3-30, 3-31 and 4-3.

The invention claimed is:
1. A substituted anilide derivative represented by general formula (I-1):

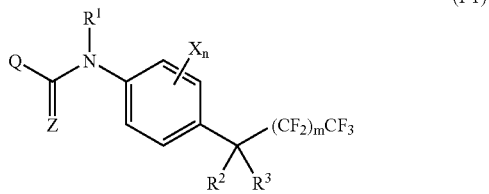

(I-1)

{wherein $R^1$ is a hydrogen atom, a $(C_1-C_6)$alkyl group, a halo$(C_1-C_6)$alkyl group, a $(C_1-C_6)$alkylcarbonyl group or a halo$(C_1-C_6)$alkylcarbonyl group,
$R^2 = CF_3$
$R^3$ is a hydrogen atom, a halogen atom, a $(C_1-C_6)$alkyl group, a halo$(C_1-C_6)$alkyl group, a cyano group, a hydroxyl group, a $(C_1-C_6)$alkoxy group, a halo$(C_1-C_6)$alkoxy group, a $(C_1-C_6)$alkoxy$(C_1-C_3)$alkoxy group, a halo$(C_1-C_6)$alkoxy$(C_1-C_3)$alkoxy group, a $(C_1-C_6)$alkylthio$(C_1-C_3)$alkoxy group, a halo$(C_1-C_6)$alkylthio$(C_1-C_3)$alkoxy group, a $(C_1-C_6)$alkylsulfinyl$(C_1-C_3)$alkoxy group, a halo$(C_1-C_6)$alkylsulfinyl$(C_1-C_3)$alkoxy group, a $(C_1-C_6)$alkylsulfonyl$(C_1-C_3)$alkoxy group, a halo$(C_1-C_6)$alkylsulfonyl$(C_1-C_3)$alkoxy group, a mono$(C_1-C_6)$alkylamino$(C_1-C_3)$alkoxy group, a di$(C_1-C_6)$alkylamino$(C_1-C_3)$alkoxy group whose $(C_1-C_6)$alkyl groups may be the same or different, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group or a halo$(C_1-C_6)$alkylsulfonyl group,
m=0,
each of Xs, which may be the same or different, is a halogen atom, a cyano group, a $(C_1-C_8)$alkyl group, a halo$(C_1-C_8)$alkyl group, a $(C_2-C_8)$alkenyl group, a halo$(C_2-C_8)$alkenyl group, a $(C_2-C_8)$alkynyl group, a halo$(C_2-C_8)$alkynyl group, a $(C_3-C_6)$cycloalkyl group, a $(C_3-C_6)$cycloalkyl$(C_1-C_6)$alkyl group, a $(C_1-C_8)$alkoxy group, a halo$(C_1-C_8)$alkoxy group, a $(C_1-C_6)$alkylthio group, a $(C_1-C_6)$alkylsulfinyl group, a $(C_1-C_6)$alkylsulfonyl group, a mono$(C_1-C_6)$alkylamino group, a di$(C_1-C_6)$alkylamino group whose $(C_1-C_6)$alkyl groups may be the same or different, a $(C_1-C_8)$alkylcarbonyl group, a halo$(C_1-C_8)$alkylcarbonyl group, a $(C_1-C_8)$alkylthiocarbonyl group, a halo$(C_1-C_8)$alkylthiocarbonyl group, a $(C_1-C_6)$alkylcarbonyl$(C_1-C_6)$alkyl group, a halo$(C_1-C_6)$alkylcarbonyl$(C_1-C_6)$alkyl group, a $(C_1-C_6)$alkylthiocarbonyl$(C_1-C_6)$alkyl group, a halo$(C_1-C_6)$alkylthiocarbonyl$(C_1-C_6)$alkyl group, a $(C_1-C_6)$alkoxy$(C_1-C_6)$alkyl group, a halo$(C_1-C_6)$alkoxy$(C_1-C_6)$alkyl group, a $(C_1-C_6)$alkylthio$(C_1-C_6)$alkyl group, a $(C_1-C_6)$alkylsulfinyl$(C_1-C_6)$alkyl group, a $(C_1-C_6)$alkylsulfonyl$(C_1-C_6)$alkyl group, a mono$(C_1-C_6)$alkylamino$(C_1-C_6)$alkyl group, a di$(C_1-C_6)$alkylamino$(C_1-C_6)$alkyl group in which the $(C_1-C_6)$alkyl groups of the di$(C_1-C_6)$alkylamino group may be the same or different, a phenyl group, or a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups, n is an integer of 1 to 4, further, two adjacent Xs on the aromatic ring being able to be taken together to represent a fused ring that may have one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups, and X being able to bind to $R^1$ to form a 5- to 8-membered ring that may contain one or two atoms which may be the same or different and are selected from oxygen atom, sulfur atom and nitrogen atom, between adjacent carbon atoms constituting the ring, Z is an oxygen atom or a sulfur atom, and
Q is a substituent represented by the formula Q9:

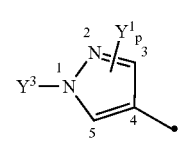

Q9

(wherein each of $Y^1$s, which may be the same or different, is a halogen atom; a cyano group; a nitro group; a $(C_1-C_6)$alkyl group; a halo$(C_1-C_6)$alkyl group; a $(C_2-C_6)$alkenyl group; a halo$(C_2-C_6)$alkenyl group; a $(C_2-C_6)$alkynyl group; a halo$(C_2-C_6)$alkynyl group; a $(C_1-C_6)$alkoxy group; a halo$(C_1-C_6)$alkoxy group; a $(C_1-C_6)$ alkylthio group; a halo($C_1$-$C_6$)alkylthio group; a ($C_1$-$C_6$)alkylsulfinyl group; a halo($C_1$-$C_6$)alkylsulfinyl group; a ($C_1$-$C_6$)alkylsulfonyl group; a halo($C_1$-$C_6$)alkylsulfonyl group; a mono($C_1$-$C_6$)alkylamino group; a di($C_1$-$C_6$)alkylamino group whose ($C_1$-$C_6$)alkyl groups may be the same or different; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenoxy group; a substituted phenoxy group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, further, two adjacent $Y^1$s on the aromatic ring being able to be taken together to represent a fused ring that may have one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, $Y^3$ is a hydrogen atom, a ($C_1$-$C_6$)alkyl group, a halo($C_1$-$C_6$)alkyl group, a phenyl group, or a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, p is an integer of 0 to 2)}.

2. A substituted anilide derivative represented by general formula (I-2):

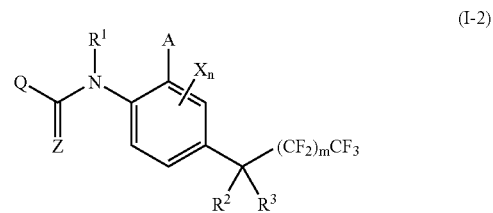

(I-2)

{wherein $R^1$ is a hydrogen atom, a ($C_1$-$C_6$)alkyl group or a halo($C_1$-$C_6$)alkyl group, $R^2$ =$CF_3$, $R^3$ is a hydrogen atom, a halogen atom, a hydroxyl group, a ($C_1$-$C_6$ alkoxy group, a halo($C_1$-$C_6$)alkoxy group, a ($C_1$-$C_6$)alkoxy($C_1$-$C_3$)alkoxy group, a halo($C_1$-$C_6$)alkoxy($C_1$-$C_3$)alkoxy group, a ($C_1$-$C_6$)alkylthio($C_1$-$C_3$)alkoxy group, a ($C_1$-$C_6$)alkylsulfinyl($C_1$-$C_3$)alkoxy group, a ($C_1$-$C_6$)alkylsulfonyl($C_1$-$C_3$)alkoxy group, a mono($C_1$-$C_6$)alkylamino($C_1$-$C_3$)alkoxy group, a di($C_1$-$C_6$)alkylamino($C_1$-$C_3$)alkoxy group whose ($C_1$-$C_6$)alkyl groups may be the same or different, a ($C_1$-$C_6$)alkylthio group, a halo($C_1$-$C_6$)alkylthio group, a ($C_1$-$C_6$)alkylsulfinyl group, a halo($C_1$-$C_6$)alkylsulfinyl group, a ($C_1$-$C_6$)alkylsulfonyl group or a halo($C_1$-$C_6$)alkylsulfonyl group, m =0, A is a ($C_3$-$C_8$)alkyl group, a halo($C_3$-$C_8$)alkyl group, a ($C_3$-$C_8$)alkenyl group, a halo($C_3$-$C_8$)alkenyl group, a ($C_3$-$C_8$)alkynyl group, a halo($C_3$-$C_8$)alkynyl group, a ($C_3$-$C_6$)cycloalkyl group, a ($C_3$-$C_6$)cycloalkyl($C_1$-$C_6$)alkyl group, a phenyl group, or a substituted phenyl group having one or more substituent which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, each of Xs, which may be the same or different, is a halogen atom, a cyano group, a ($C_1$-$C_8$)alkyl group, a halo($C_1$-$C_8$)alkyl group, a ($C_2$-$C_8$)alkenyl group, a halo($C_2$-$C_8$)alkenyl group, a ($C_2$-$C_8$)alkynyl group, a halo($C_2$-$C_6$)alkynyl group, a ($C_3$-$C_6$)cycloalkyl group, a ($C_3$-$C_6$)cycloalkyl($C_1$-$C_6$)alkyl group, a ($C_1$-$C_8$)alkoxy group, a halo($C_1$-$C_8$)alkoxy group, a ($C_1$-$C_6$)alkylthio group, a ($C_1$-$C_6$)alkylsulfinyl group, a ($C_1$-$C_6$)alkylsulfonyl group, a mono($C_1$-$C_6$)alkylamino group, a di($C_1$-$C_6$)alkylamino group whose ($C_1$-$C_6$)alkyl groups may be the same or different, a ($C_1$-$C_6$)alkylcarbonyl($C_1$-$C_6$)alkyl group, a halo($C_1$-$C_6$)alkylcarbonyl($C_1$-$C_6$)alkyl group, a ($C_1$-$C_6$)alkylthiocarbonyl($C_1$-$C_6$)alkyl group, a ($C_1$-$C_6$)alkoxy($C_1$-$C_6$)alkyl group, a halo($C_1$-$C_6$)alkoxy($C_1$-$C_6$)alkyl group, a ($C_1$-$C_6$)alkylthio($C_1$-$C_6$)alkyl group, a ($C_1$-$C_6$)alkylsulfinyl($C_1$-$C_6$)alkyl group, a ($C_1$-$C_6$)alkylsulfonyl($C_1$-$C_6$)alkyl group, a mono($C_1$-$C_6$)alkylamino($C_1$-$C_6$)alkyl group, or a di($C_1$-$C_6$)akylamino($C_1$-$C_6$)alkyl group in which the ($C_1$-$C_6$)alkyl groups of the di($C_1$-$C_6$)alkylamino group may be the same or different, n is an integer of 0 to 3, Z is an oxygen atom, and Q is a substituent represented by the formula Q9:

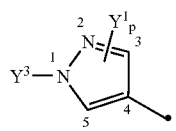

(wherein each of $Y^1$s, which may be the same or different, is a halogen atom; a cyano group; a nitro group; a ($C_1$-$C_6$)alkyl group; halo($C_1$-$C_6$)alkyl group; a ($C_2$-$C_6$)alkenyl group; a halo $C_2$-$C_6$)alkenyl group; a ($C_2$-$C_6$)alkynyl group; a halo($C_2$-$C_6$)alkynyl group; a ($C_1$-$C_6$)alkoxy group; a halo($C_1$-$C_6$ alkoxy group; a ($C_1$-$C_6$)alkylthio group; a halo($C_1$-$C_6$)alkylthio group; a ($C_1$-$C_6$)alkylsulfinyl group; a halo($C_1$-$C_6$)alkylsulfinyl group; a ($C_1$-$C_6$)alkylsulfonyl group; a halo($C_1$-$C_6$)alkylsulfonyl group; a mono($C_1$-$C_6$)alkylamino group; a di($C_1$-$C_6$)alkylamino group whose ($C_1$-$C_6$)alkyl groups may be the same or different; a phenyl group, a substituted phenyl group having one or more substituents which may be the same or different and are selected from halogen atoms, cyano group, nitro group, ($C_1$-$C_6$ alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$) alkylamino groups, di($C_1$-$C_6$)alkylamino groups whose ($C_1$-$C_6$)alkyl groups may be the same or different, and ($C_1$-$C_6$alkoxycarbonyl groups; a phenoxy group; a substituted phenoxy group having one or more substituents which may be the same or different and are selected from halogen atoms, cyano group, nitro group, ($C_1$-$C_6$)alkyl groups, halo $C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino group, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)-alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, further, two adjacent $Y^1$s on the aromatic ring being able to be taken together to represent a fused ring that may have one or more substituents which may be the same or different and are selected from halogen atoms, cyano group, nitro group, ($C_1$-$C_6$)alkyl groups, halo($C_1$-$C_6$) alkyl groups, ($C_1$-$C_6$alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, $Y^3$ is a hydrogen atom, a ($C_1$-$C_6$)alkyl group, a halo($C_1$-$C_6$)alkyl group, a phenyl group, or a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$) alkoxy groups, ($C_1$-$C_6$)alkylthio groups, halo($C_1$-$C_6$) alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, p is an integer of 0 to 2)}.

3. An agricultural and horticultural insecticidal composition comprising an insecticidally effective amount of 0.01 g to 1 kg per 10 ares of a substituted anilide derivative represented by general formula (I-1):

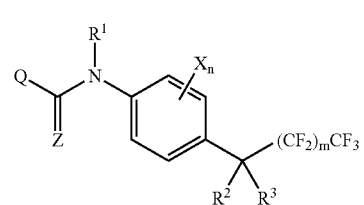

{wherein $R^1$ is a hydrogen atom, a ($C_1$-$C_6$)alkyl group, a halo($C_1$-$C_6$)alkyl group, a ($C_1$-$C_6$)alkylcarbonyl group or a halo($C_1$-$C_6$)alkylcarbonyl group, $R^2$ is a hydrogen atom, a halogen atom or a halo($C_1$-$C_6$) alkyl group, $R^3$ is a hydrogen atom, a halogen atom, a ($C_1$-$C_6$)alkyl group, a halo($C_1$-$C_6$)alkyl group, a cyano group, a hydroxyl group, a ($C_1$-$C_6$)alkoxy group, a halo($C_1$-$C_6$) alkoxy group, a ($C_1$-$C_6$)alkoxy($C_1$-$C_3$)alkoxy group, a halo($C_1$-$C_6$)alkoxy($C_{1-3}$)alkoxy group, a ($C_1$-$C_6$)alkylthio($C_1$-$C_3$)alkoxy group, a halo($C_1$-$C_6$)alkylthio($C_1$-$C_3$)alkoxy group, a ($C_1$-$C_6$)alkylsulfinyl($C_1$-$C_3$)alkoxy group, a halo($C_1$-$C_6$)alkylsulflnyl($C_1$-$C_3$)alkoxy group, a ($C_1$-$C_6$)alkylsulfonyl($C_1$-$C_3$)alkoxy group, a halo($C_1$-$C_6$)alkylsulfonyl($C_1$-$C_3$)alkoxy group, a mono($C_1$-$C_6$)alkylamino($C_1$-$C_3$)alkoxy group, a di($C_1$-$C_6$)alkylamino($C_1$-$C_3$)alkoxy group whose ($C_1$-$C_6$)alkyl groups may be the same or different, a ($C_1$-$C_6$)alkylthio group, a halo($C_1$-$C_6$)alkylthio group, a ($C_1$-$C_6$)alkylsulfinyl group, a halo($C_1$-$C_6$)alkylsulfinyl group, a ($C_1$-$C_6$) alkylsulfonyl group or a halo($C_1$-$C_6$)alkylsulfonyl group, m is an integer of 0 to 6, each of Xs, which may be the same or different, is a halogen atom, a cyano group, a ($C_1$-$C_8$)alkyl group, a halo($C_1$-$C_8$)alkyl group, a ($C_2$-$C_8$)alkenyl group, a halo($C_2$-$C_8$) alkenyl group, a ($C_2$-$C_8$)alkynyl group, a halo($C_2$-$C_8$) alkynyl group, a ($C_3$-$C_6$)cycloalkyl group, a ($C_3$-$C_6$) cycloalkyl($C_1$-$C_6$)alkyl group, a ($C_1$-$C_8$)alkoxy group, a halo($C_1$-$C_8$)alkoxy group, a ($C_1$-$C_6$)alkylthio group, a ($C_1$-$C_6$)alkylsulfinyl group, a ($C_{1-6}$)alkylsulfonyl group, a mono($C_1$-$C_6$)alkylamino group, a di($C_1$-$C_6$)alkylamino group whose ($C_{1-6}$)alkyl groups may be the same or different, a ($C_1$-$C_8$)alkylcarbonyl group, a halo($C_1$-$C_8$)alkylcarbonyl group, a ($C_1$-$C_8$)alkylthiocarbonyl group, a halo($C_1$-$C_8$)alkylthiocarbonyl group, a ($C_1$-$C_6$)alkylcarbonyl($C_1$-$C_6$)alkyl group, a halo($C_1$-$C_6$)alkylcarbonyl($C_1$-$C_6$)alkyl group, a ($C_1$-$C_6$)alkylthiocarbonyl($C_1$-$C_6$)alkyl group, a halo($C_1$-$C_6$)alkylthiocarbonyl($C_1$-$C_6$)alkyl group, a ($C_1$-$C_6$)alkoxy($C_1$-$C_6$)alkyl group, a halo($C_1$-$C_6$)alkoxy($C_1$-$C_6$)alkyl group, a ($C_1$-$C_6$)alkylthio($C_1$-$C_6$)alkyl group, a ($C_1$-$C_6$)alkylsulfinyl($C_1$-$C_6$)alkyl group, a ($C_1$-$C_6$)alkylsulfonyl($C_1$-$C_6$)alkyl group, a mono($C_1$-$C_6$)alkylamino($C_1$-$C_6$)alkyl group, a di($C_1$-$C_6$)alkylamino($C_1$-$C_6$)alkyl group in which the ($C_1$-$C_6$)alkyl groups of the di($C_1$-$C_6$)akylamino group may be the same or different, a phenyl group, or a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, n is an integer of 1 to 4, further, two adjacent Xs on the aromatic ring being able to be taken together to represent a fused ring that may have one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, and X being able to bind to $R^1$ to form a 5- to 8-membered ring that may contain one or two atoms which may be the same or different and are selected from oxygen atom, sulfur atom and nitrogen atom, between adjacent carbon atoms constituting the ring, Z is an oxygen atom, and Q is a substituent represented by the Q9

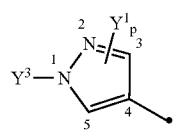

Q9

(wherein each of $Y^1$s, which may be the same or different, is a halogen atom; a cyano group; a nitro group; a ($C_1$-$C_6$)alkyl group; a halo($C_1$-$C_6$)alkyl group; a ($C_{2-6}$)alkenyl group; a halo($C_2$-$C_6$)alkenyl group; a ($C_2$-$C_6$)alkynyl group; a halo($C_2$-$C_6$)alkynyl group; a ($C_1$-$C_6$)alkoxy group; a halo($C_1$-$C_6$)alkoxy group; a ($C_1$-$C_6$)alkylthio group; a halo($C_1$-$C_6$)alkylthio group; a ($C_1$-$C_6$)alkylsulfinyl group; a halo($C_1$-$C_6$)alkylsulfinyl group; a ($C_1$-$C_6$)alkylsulfonyl group; a halo($C_1$-$C_6$)alkylsulfonyl group; a mono($C_1$-$C_6$)alkylamino group; a di($C_1$-$C_6$)alkylamino group whose ($C_1$-$C_6$)alkyl groups may be the same or different; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_{1-6}$)alkylamino groups, di($C_1$-$C_6$)alkylamino groups whose ($C_1$-$C_6$)alkyl groups may be the same or different, and ($C_1$-$C_6$)alkoxycarbonyl groups; a phenoxy group; a substituted phenoxy group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_{1-6}$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, further, two adjacent $Y^1$s on the aromatic ring being able to be taken together to represent a fused ring that may have one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, $Y^3$ is a hydrogen atom, a ($C_1$-$C_6$)alkyl group, a halo($C_1$-$C_6$)alkyl group, a phenyl group, or a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, p is an integer of 0 to 2)}.

4. The agricultural and horticultural insecticidal composition according to claim 3, wherein the substituted anilide derivative is represented by general formula (I-2):

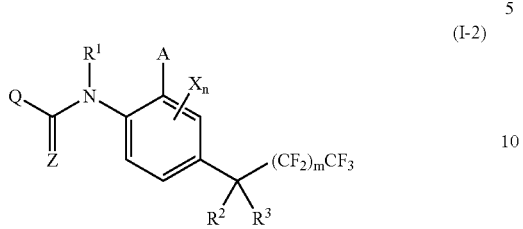
(I-2)

{wherein $R^1$ is a hydrogen atom, a $(C_1-C_6)$alkyl group or a halo$(C_1-C_6)$alkyl group, $R^2$ is a hydrogen atom, a halogen atom or a halo$(C_1-C_6)$alkyl group, $R^3$ is a hydrogen atom, a halogen atom, a hydroxyl group, a $(C_1-C_6)$alkoxy group, a halo$(C_1-C_6)$alkoxy group, a $(C_1-C_6)$alkoxy$(C_1-C_3)$alkoxy group, a halo$(C_1-C_6)$alkoxy$(C_1-C_3)$alkoxy group, a $(C_1-C_6)$alkylthio$(C_1-C_3)$alkoxy group, a $(C_1-C_6)$alkylsulfinyl$(C_1-C_3)$alkoxy group, a $(C_1-C_6)$alkylsulfonyl$(C_1-C_3)$alkoxy group, a mono$(C_1-C_6)$alkylamino$(C_1-C_3)$alkoxy group, a di$(C_1-C_6)$alkylamino$(C_1-C_3)$alkoxy group whose $(C_1-C_6)$alkyl groups may be the same or different, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group or a halo$(C_1-C_6)$alkylsulfonyl group, m is an integer of 0 to 6, A is a $(C_3-C_8)$alkyl group, a halo$(C_3-C_8)$alkyl group, a $(C_3-C_8)$alkenyl group, a halo$(C_3-C_8)$alkenyl group, a $(C_3-C_8)$alkynyl group, a halo$(C_3-C_8)$alkynyl group, a $(C_3-C_6)$cycloalkyl group, a $(C_3-C_6)$cycloalkyl$(C_1-C_6)$alkyl group, a phenyl group, or a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups, each of Xs, which may be the same or different, is a halogen atom, a cyano group, a $(C_1-C_8)$alkyl group, a halo$(C_1-C_8)$alkyl group, a $(C_2-C_8)$alkenyl group, a halo$(C_2-C_8)$alkenyl group, a $(C_2-C_8)$alkynyl group, a halo$(C_2-C_8)$alkynyl group, a $(C_3-C_6)$cycloalkyl group, a $(C_3-C_6)$cycloalkyl$(C_1-C_6)$alkyl group, a $(C_1-C_8)$alkoxy group, a halo$(C_1-C_8)$alkoxy group, a $(C_1-C_6)$alkylthio group, a $(C_1-C_6)$alkylsulfinyl group, a $(C_1-C_6)$alkylsulfonyl group, a mono$(C_1-C_6)$alkylamino group, a di$(C_1-C_6)$alkylamino group whose $(C_1-C_6)$alkyl groups may be the same or different, a $(C_1-C_6)$alkylcarbonyl$(C_1-C_6)$alkyl group, a halo$(C_1-C_6)$alkylcarbonyl$(C_1-C_6)$alkyl group, a $(C_1-C_6)$alkylthiocarbonyl$(C_1-C_6)$alkyl group, a $(C_1-C_6)$alkoxy$(C_1-C_6)$alkyl group, a halo$(C_1-C_6)$alkoxy$(C_1-C_6)$alkyl group, a $(C_1-C_6)$alkylthio$(C_1-C_6)$alkyl group, a $(C_1-C_6)$alkylsulfinyl$(C_1-C_6)$alkyl group, a $(C_1-C_6)$alkylsulfonyl$(C_1-C_6)$alkyl group, a mono$(C_1-C_6)$alkylamino$(C_1-C_6)$alkyl group, or a di$(C_1-C_6)$alkylamino$(C_1-C_6)$alkyl group in which the $(C_1-C_6)$alkyl groups of the di$(C_1-C_6)$alkylamino group may be the same or different, n is an integer of 0 to 3, Z is an oxygen atom, and Q is a substituent represented by the formula Q9:

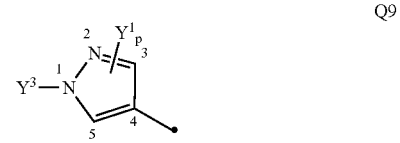
Q9

(wherein each of $Y^1$s, which may be the same or different, is a halogen atom; a cyano group; a nitro group; a $(C_1-C_6)$alkyl group; a halo$(C_1-C_6)$alkyl group; a $(C_2-C_6)$alkenyl group; a halo$(C_2-C_6)$alkenyl group; a $(C_2-C_6)$alkynyl group; a halo$(C_2-C_6)$alkynyl group; a $(C_1-C_6)$alkoxy group; a halo$(C_1-C_6)$alkoxy group; a $(C_1-C_6)$alkylthio group; a halo$(C_1-C_6)$alkylthio group; a $(C_1-C_6)$alkylsulfinyl group; a halo$(C_1-C_6)$alkylsulfinyl group; a $(C_1-C_6)$alkylsulfonyl group; a halo$(C_1-C_6)$alkylsulfonyl group; a mono$(C_1-C_6)$alkylamino group; a di$(C_1-C_6)$alkylamino group whose $(C_1-C_6)$alkyl groups may be the same or different; a phenyl group; a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_{1-6})$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a phenoxy group; a substituted phenoxy group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups; a heterocyclic group; or a substituted heterocyclic group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$alkyl groups may be the same or different, and $(C_1-C_6)$alkoxycarbonyl groups, further, two adjacent $Y^1$s on the aromatic ring being able to be taken together to represent a fused ring that may have one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$ alkyl groups may be the same or different, and $(C_1-C_6)$ alkoxy-carbonyl groups, $Y^3$ is a hydrogen atom, a $(C_1-C_6)$alkyl group, a halo$(C_1-C_6)$alkyl group, a phenyl group, or a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_{1-6})$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_{1-6})$alkylamino groups, di$(C_1-C_6)$alkylamino groups whose $(C_1-C_6)$alkyl groups may be the same or different, and $(C_1-C_6)$alkoxycarbonyl groups, p is an integer of 0 to 2)}.

5. A method for applying an agricultural and horticultural insecticide, comprising the steps of applying an agricultural and horticultural insecticide including a substituted anilide derivative as an active ingredient to a plant to be protected or soil in an effective dosage for protecting useful plants against pests, wherein the substituted anilide derivative is represented by general formula (I-1):

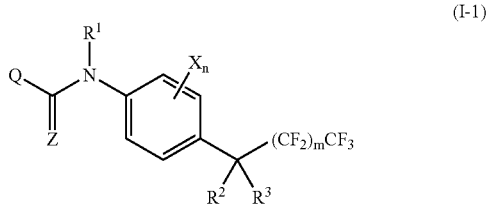

(I-1)

{wherein $R^1$ is a hydrogen atom, a $(C_1-C_6)$alkyl group, a halo$(C_1-C_6)$alkyl group, a $(C_1-C_6)$alkylcarbonyl group or a halo$(C_1-C_6)$alkylcarbonyl group, $R^2$ is a hydrogen atom, a halogen atom or a halo$(C_1-C_6)$ alkyl group, $R^3$ is a hydrogen atom, a halogen atom, a $(C_1-C_6)$alkyl group, a halo$(C_1-C_6)$alkyl group, a cyano group, a hydroxyl group, a $(C_1-C_6)$alkoxy group, a halo$(C_1-C_6)$alkoxy group, a $(C_{1-6})$alkoxy$(C_1-C_3)$alkoxy group, a halo$(C_1-C_6)$alkoxy$(C_1-C_3)$alkoxy group, a $(C_1-C_6)$alkylthio$(C_1-C_3)$alkoxy group, a halo$(C_1-C_6)$alkylthio$(C_1-C_3)$alkoxy group, a $(C_1-C_6)$alkylsulfinyl$(C_1-C_3)$alkoxy group, a halo$(C_1-C_6)$alkylsulfinyl$(C_1-C_3)$alkoxy group, a $(C_1-C_6)$alkylsulfonyl$(C_1-C_3)$alkoxy group, a halo$(C_1-C_6)$alkylsulfonyl$(C_1-C_3)$alkoxy group, a mono$(C_1-C_6)$alkylamino$(C_1-C_3)$alkoxy group, a di$(C_1-C_6)$alkylamino$(C_1-C_3)$alkoxy group whose $(C_1-C_6)$alkyl groups may be the same or different, a $(C_1-C_6)$alkylthio group, a halo$(C_{1-6})$alkylthio group, a $(C_1-C_6)$alkylsulfinyl group, a halo$(C_1-C_6)$alkylsulfinyl group, a $(C_1-C_6)$alkylsulfonyl group or a halo$(C_1-C_6)$alkylsulfonyl group, m is an integer of 0 to 6, each of Xs, which may be the same or different, is a halogen atom, a cyano group, a $(C_1-C_8)$alkyl group, a halo$(C_1-C_8)$alkyl group, a $(C_2-C_8)$alkenyl group, a halo$(C_2-C_8)$ alkenyl group, a $(C_2-C_8)$alkynyl group, a halo$(C_2-C_8)$ alkynyl group, a $(C_3-C_6)$cycloalkyl group, a $(C_3-C_6)$ cycloalkyl$(C_1-C_6)$alkyl group, a $(C., -C_8)$alkoxy group, a halo$(C_{1-8})$alkoxy group, a $(C_1-C_6)$alkylthio group, a $(C_1-C_6)$alkylsulfinyl group, a $(C_1-C_6)$alkylsulfonyl group, a mono$(C_1-C_6)$alkylamino group, a di$(C_1-C_6)$ alkylamino group whose $(C_1-C_6)$alkyl groups may be the same or different, a $(C_1-C_8)$alkylcarbonyl group, a halo$(C_1-C_8)$alkylcarbonyl group, a $(C_1-C_8)$alkylthiocarbonyl group, a halo$(C_1-C_8)$alkylthiocarbonyl group, a $(C_1-C_6)$alkylcarbonyl$(C_1-C_6)$alkyl group, a halo$(C_1-C_6)$ alkylcarbonyl$(C_1-C_6)$alkyl group, a $(C_1-C_6)$alkylthiocarbonyl$(C_1-C_6)$alkyl group, a halo$(C_1-C_6)$alkylthiocarbonyl$(C_1-C_6)$alkyl group, a $(C_1-C_6)$alkoxy$(C_1-C_6)$alkyl group, a halo$(C_1-C_6)$alkoxy$(C_1-C_6)$alkyl group, a $(C_1-C_6)$alkylthio$(C_1-C_6)$alkyl group, a $(C_1-C_6)$alkylsulfinyl $(C_1-C_6)$alkyl group, a $(C_1-C_6)$alkylsulfonyl$(C_1-C_6)$ alkyl group, a mono$(C_1-C_6)$alkylamino$(C_1-C_6)$alkyl group, a di$(C_1-C_6)$alkylamino$(C_1-C_6)$alkyl group in which the $(C_1-C_6)$alkyl groups of the di$(C_1-C_6)$akylamino group may be the same or different, a phenyl group, or a substituted phenyl group having one or more substituents which may be the same or different and are selected from halogen atoms, cyano group, nitro group, $(C_1-C_6)$alkyl groups, halo$(C_1-C_6)$alkyl groups, $(C_1-C_6)$ alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$ alkylamino groups whose $(C_1-C_6)$alkyl groups may be the same or different, and $(C_1-C_6)$alkoxycarbonyl groups, n is an integer of 1 to 4 further, two adjacent Xs on the aromatic ring being able to be taken together to represent a fused ring that may have one or more substituents which may be the same or different and are selected from halogen atoms, cyano group, nitro group, $(C_1-C_6)$alkyl groups, halo$(C_1-C_6)$ alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups whose $(C_1-C_6)$ alkyl groups may be the same or different, and $(C_1-C_6)$ alkoxycarbonyl groups, and X being able to bind to $R^1$ to form a 5- to 8-membered ring that may contain one or two atoms which may be the same or different and are selected from oxygen atom, sulfur atom and nitrogen atom, between adjacent carbon atoms constituting the ring, Z is an oxygen atom, and Q is a substituent represented by the formula Q9:

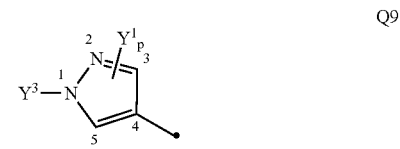

Q9

(wherein each of $Y^1$ s, which may be the same or different, is a halogen atom; a cyano group; a nitro group; a $(C_1-C_6)$alkyl group; a halo$(C_1-C_6)$alkyl group; a $(C_2-C_6)$ alkenyl group; a halo$(C_2-C_6)$alkenyl group; a $(C_2-C_6)$ alkynyl group; a halo($C_2$-$C_6$)alkynyl group; a ($C_1$-$C_6$) alkoxy group; a halo($C_1$-$C_6$)alkoxy group; a ($C_1$-$C_6$) alkylthio group; a halo($C_1$-$C_6$)alkylthio group; a ($C_1$-$C_6$)alkylsulfinyl group; a halo($C_1$-$C_6$)alkylsulfinyl group; a ($C_1$-$C_6$)alkylsulfonyl group; a halo($C_1$-$C_6$) alkylsulfonyl group; a mono($C_1$-$C_6$)alkylamino group; a di($C_1$-$C_6$)alkylamino group whose ($C_1$-$C_6$)alkyl groups may be the same or different; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_{1\text{-}6}$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$) alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenoxy group; a substituted phenoxy group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$) alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, further, two adjacent $Y^1$s on the aromatic ring being able to be taken together to represent a fused ring that may have one or more substituents which may be the same or different and are selected from halogen atoms, cyano group, nitro group, ($C_1$-$C_6$)alkyl groups, halo($C_1$-$C_6$) alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$) alkyl groups may be the same or different, and ($C_1$-$C_6$) alkoxycarbonyl groups, $Y^3$ is a hydrogen atom, a ($C_1$-$C_6$)alkyl group, a halo($C_1$-$C_6$)alkyl group, a phenyl group, or a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$) alkoxy groups, ($C_1$-$C_6$)alkylthio groups, halo($C_1$-$C_6$) alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, p is an integer of 0 to 2)}.

6. The method according to claim 5, wherein the substituted anilide derivative is represented by general formula (I-2):

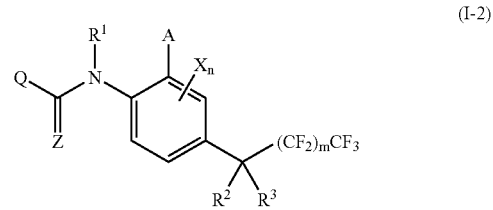

(I-2)

{wherein $R^1$ is a hydrogen atom, a ($C_1$-$C_6$)alkyl group or a halo($C_1$-$C_6$)alkyl group, $R^2$ is a hydrogen atom, a halogen atom or a halo($C_1$-$C_6$) alkyl group, $R^3$ is a hydrogen atom, a halogen atom, a hydroxyl group, a ($C_1$-$C_6$)alkoxy group, a halo($C_1$-$C_6$)alkoxy group, a ($C_1$-$C_6$)alkoxy($C_1$-$C_3$)alkoxy group, a halo($C_1$-$C_6$) alkoxy($C_1$-$C_3$)alkoxy group, a ($C_1$-$C_6$)alkylthio($C_1$-$C_3$) alkoxy group, a ($C_1$-$C_6$)alkylsulfinyl($C_1$-$C_3$)alkoxy group, a ($C_1$-$C_6$)alkylsulfonyl($C_1$-$C_3$)alkoxy group, a mono($C_1$-$C_6$)alkylamino($C_1$-$C_3$)alkoxy group, a di($C_1$-$C_6$)alkylamino($C_1$-$C_3$)alkoxy group whose ($C_1$-$C_6$) alkyl groups may be the same or different, a ($C_1$-$C_6$) alkylthio group, a halo($C_1$-$C_6$)alkylthio group, a ($C_1$-$C_6$) alkylsulfinyl group, a halo($C_1$-$C_6$)alkylsulfinyl group, a ($C_1$-$C_6$)alkylsulfonyl group or a halo($C_1$-$C_6$)alkylsulfonyl group, m is an integer of 0 to 6, A is a ($C_3$-$C_8$)alkyl group, a halo($C_3$-$C_8$)alkyl group, a ($C_3$-$C_8$)alkenyl group, a halo($C_3$-$C_8$)alkenyl group, a ($C_3$-$C_8$)alkynyl group, a halo($C_3$-$C_8$)alkynyl group, a ($C_3$-$C_6$)cycloalkyl group, a ($C_3$-$C_6$)cycloalkyl($C_1$-$C_6$) alkyl group, a phenyl group, or a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$) alkoxy groups, ($C_1$-$C_6$)alkylthio groups, halo($C_1$-$C_6$) alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, each of Xs, which may be the same or different, is a halogen atom, a cyano group, a ($C_1$-$Ca$)alkyl group, a halo($C_1$-$C_8$)alkyl group, a ($C_2$-$C_8$)alkenyl group, a halo($C_{2\text{-}8}$) alkenyl group, a ($C_2$-$C_8$)alkynyl group, a halo($C_2$-$C_8$) alkynyl group, a ($C_3$-$C_6$)cycloalkyl group, a ($C_3$-$C_6$) cycloalkyl($C_1$-$C_6$)alkyl group, a ($C_1$-$C_8$)alkoxy group, a halo($C_1$-$C_8$)alkoxy group, a ($C_1$-$C_6$)alkylthio group, a ($C_1$-$C_6$)alkylsulfinyl group, a ($C_1$-$C_6$)alkylsulfonyl group, a mono($C_1$-$C_6$)alkylamino group, a di($C_1$-$C_6$) alkylamino group whose ($C_1$-$C_6$)alkyl groups may be the same or different, a ($C_1$-$C_6$)alkylcarbonyl($C_1$-$C_6$) alkyl group, a halo($C_1$-$C_6$)alkylcarbonyl($C_1$-$C_6$)alkyl group, a ($C_1$-$C_6$)alkylthiocarbonyl($C_1$-$C_6$)alkyl group, a ($C_1$-$C_6$)alkoxy($C_1$-$C_6$)alkyl group, a halo($C_1$-$C_6$)alkoxy ($C_1$-$C_6$)alkyl group, a ($C_1$-$C_6$)alkylthio($C_1$-$C_6$)alkyl group, a ($C_1$-$C_6$)alkylsulfinyl($C_1$-$C_6$)alkyl group, a ($C_1$-$C_6$)alkylsulfonyl($C_1$-$C_6$)alkyl group, a mono($C_1$-$C_6$)alkylamino($C_1$-$C_6$)alkyl group, or a di($C_1$-$C_6$)alkylamino($C_1$-$C_6$)alkyl group in which the ($C_1$-$C_6$)alkyl groups of the di($C_1$-$C_6$)alkylamino group may be the same or different, n is an integer of 0 to 3, Z is an oxygen atom, and Q is a substituent represented by the formula Q9:

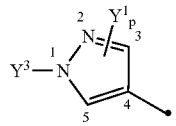

Q9

(wherein each of $Y^1$ s, which may be the same or different, is a halogen atom; a cyano group; a nitro group; a ($C_1$-$C_6$)alkyl group; a halo($C_1$-$C_6$)alkyl group; a ($C_2$-$C_6$)alkenyl group; a halo($C_2$-$C_6$)alkenyl group; a ($C_2$-$C_6$)alkynyl group; a halo($C_2$-$C_6$)alkynyl group; a ($C_1$-$C_6$)alkoxy group; a halo($C_1$-$C_6$)alkoxy group; a ($C_1$-$C_6$)alkylthio group; a halo($C_1$-$C_6$)alkylthio group; a ($C_1$-$C_6$)alkylsulfinyl group; a halo($C_1$-$C_6$)alkylsulfinyl group; a ($C_1$-$C_6$)alkylsulfonyl group; a halo($C_1$-$C_6$)alkylsulfonyl group; a mono($C_1$-$C_6$)alkylamino group; a di($C_1$-$C_6$)alkylamino group whose ($C_1$-$C_6$)alkyl groups may be the same or different; a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_{1-6}$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a phenoxy group; a substituted phenoxy group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups; a heterocyclic group; or a substituted heterocyclic group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, further, two adjacent $Y^1$s on the aromatic ring being able to be taken together to represent a fused ring that may have one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxy-carbonyl groups, $Y^3$ is a hydrogen atom, a ($C_1$-$C_6$)alkyl group, a halo($C_1$-$C_6$)alkyl group, a phenyl group, or a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups, halo($C_1$-$C_6$)alkoxy groups, ($C_1$-$C_6$)alkylthio groups, halo($C_1$-$C_6$)alkylthio groups, ($C_1$-$C_6$)alkylsulfinyl groups, halo($C_1$-$C_6$)alkylsulfinyl groups, ($C_1$-$C_6$)alkylsulfonyl groups, halo($C_1$-$C_6$)alkylsulfonyl groups, mono($C_1$-$C_6$)alkylamino groups, di($C_1$-$C_6$)alkylamino groups whose ($C_1$-$C_6$)alkyl groups may be the same or different, and ($C_1$-$C_6$)alkoxycarbonyl groups, p is an integer of 0 to 2)}.

* * * * *